(12) United States Patent
Weston et al.

(10) Patent No.: US 6,287,770 B1
(45) Date of Patent: Sep. 11, 2001

(54) NUCLEIC ACID PROMOTERS

(75) Inventors: Anthony Weston, Northolt; Rene Assenberg, Banbury; Peter Marsh, Leamington Spa; Graham A Mock, Thame; Trevor D. Ray, Abingdon; Susan D Wharam, Coventry; Donald L. N. Cardy, Aston Le Walls, all of (GB)

(73) Assignee: Cytocell Limited, Banbury (GB)

( * ) Notice: Subject to any disclaimer, the term of this patent is extended or adjusted under 35 U.S.C. 154(b) by 0 days.

(21) Appl. No.: 09/284,832

(22) PCT Filed: Jan. 26, 1999

(86) PCT No.: PCT/GB99/00265

§ 371 Date: Aug. 2, 1999

§ 102(e) Date: Aug. 2, 1999

(87) PCT Pub. No.: WO99/37805

PCT Pub. Date: Jul. 29, 1999

(30) Foreign Application Priority Data

Jul. 8, 1997 (GB) .................................................. 9814698
Jan. 27, 1998 (GB) .................................................. 9801627

(51) Int. Cl.[7] ............................ C12Q 1/68; C07H 21/04; C07H 21/00; C12P 19/34
(52) U.S. Cl. ........................... 435/6; 435/91.1; 435/91.2; 536/22.1; 536/23.1; 536/24.1; 536/24.3; 536/24.33
(58) Field of Search .............................. 435/91.1, 91.2, 435/810; 536/22.1, 23.1, 24.1, 24.2, 24.3, 24.33; 935/77, 78; 455/6

(56) References Cited

U.S. PATENT DOCUMENTS 5,766,849 * 6/1998 McDonough et al. ................... 435/6
6,057,299 * 5/2000 Henderson ............................. 514/44

FOREIGN PATENT DOCUMENTS

| 0 552 931 A1 | 7/1993 | (EP) . |
| 0 851 033 A1 | 7/1998 | (EP) . |
| WO 88/10315 | * 12/1988 | (WO) . |
| WO 89/04375 | * 5/1989 | (WO) . |
| WO 93/06240 | * 4/1993 | (WO) . |
| WO 94/29481 | 12/1994 | (WO) . |

* cited by examiner

Primary Examiner—Stephanie Zitomer
Assistant Examiner—Cynthia B. Wilder
(74) Attorney, Agent, or Firm—Pillsbury Winthrop LLP

(57) ABSTRACT

Disclosed is a method of detecting the presence of a nucleic acid target sequence of interest, the method comprising the steps of:

(a) adding first and second nucleic acid probes to a sample comprising the sequence of interest, so as to form a complex comprising three strands of nucleic acid, wherein the first probe comprises the full length sequence of a first strand of a double stranded promoter, the target sequence comprises an end part of a second strand of the double stranded promoter which is complementary to a part of the first strand, and the second probe comprises the rest of the second strand of the double stranded promoter which is complementary to a part of the first strand, such that a functional promoter is formed when the first probe is hybridized to both the target sequence and to the second probe;

(b) adding a polymerase which recognizes the promoter, so as to cause the de novo synthesis of nucleic acid from the promoter present in the complex; and (c) detecting directly or indirectly the de novo synthesized nucleic acid. Also disclosed is the complex formed in performance of the method defined above, and a kit for performing the method defined above.

22 Claims, 16 Drawing Sheets

SEQUENCE LISTING

<160> NUMBER OF SEQ ID NOS: 45

<210> SEQ ID NO 1
<211> LENGTH: 18
<212> TYPE: DNA
<213> ORGANISM: Bacteriophage T3
<220> FEATURE:
<221> NAME/KEY: promoter
<222> LOCATION: (1)..(18)
<223> OTHER INFORMATION: 5' TO 3'

<400> SEQUENCE: 1
aaattaaccc tcactaaa                    18

<210> SEQ ID NO 2
<211> LENGTH: 18
<212> TYPE: DNA
<213> ORGANISM: Bacteriophage T3
<220> FEATURE:
<221> NAME/KEY: promoter
<222> LOCATION: (1)..(18)
<223> OTHER INFORMATION: 5' TO 3'
<220> FEATURE:
<221> NAME/KEY: promoter
<222> LOCATION: Complement ((1)..(18))

<400> SEQUENCE: 2
tttagtgagg gttaattt                    18

<210> SEQ ID NO 3
<211> LENGTH: 17
<212> TYPE: DNA
<213> ORGANISM: Bacteriophage T7
<220> FEATURE:
<221> NAME/KEY: promoter
<222> LOCATION: (1)..(17)
<223> OTHER INFORMATION: 5' TO 3'

<400> SEQUENCE: 3
taatacgact cactata                     17

<210> SEQ ID NO 4

-continued

```
<211> LENGTH: 17
<212> TYPE: DNA
<213> ORGANISM: Bacteriophage T7
<220> FEATURE:
<221> NAME/KEY: promoter
<222> LOCATION: Complement ((1)..(17))

<400> SEQUENCE: 4
tatagtgagt cgtatta                                                 17

<210> SEQ ID NO 5
<211> LENGTH: 17
<212> TYPE: DNA
<213> ORGANISM: Bacteriophage SP6
<220> FEATURE:
<221> NAME/KEY: promoter
<222> LOCATION: (1)..(17)
<223> OTHER INFORMATION: 5' TO 3'

<400> SEQUENCE: 5
atttaggtga cactata                                                 17

<210> SEQ ID NO 6
<211> LENGTH: 17
<212> TYPE: DNA
<213> ORGANISM: Bacteriophage SP6
<220> FEATURE:
<221> NAME/KEY: promoter
<222> LOCATION: (1)..(17)
<223> OTHER INFORMATION: 3' TO 5'

<400> SEQUENCE: 6
tatagtgtca cctaaat                                                 17

<210> SEQ ID NO 7
<211> LENGTH: 12
<212> TYPE: DNA
<213> ORGANISM: Bacteriophage T7

<400> SEQUENCE: 7
gttctctctc cc                                                      12

<210> SEQ ID NO 8
<211> LENGTH: 12
<212> TYPE: DNA
<213> ORGANISM: Bacteriophage T7

<400> SEQUENCE: 8
gctctctctc cc                                                      12

<210> SEQ ID NO 9
<211> LENGTH: 12
<212> TYPE: DNA
<213> ORGANISM: Bacteriophage T7

<400> SEQUENCE: 9
gttgtgtctc cc                                                      12

<210> SEQ ID NO 10
<211> LENGTH: 12
<212> TYPE: DNA
<213> ORGANISM: Bacteriophage T7

<400> SEQUENCE: 10
gatgtgtctc cc                                                      12
```

```
<210> SEQ ID NO 11
<211> LENGTH: 12
<212> TYPE: DNA
<213> ORGANISM: Bacteriophage T7

<400> SEQUENCE: 11
atcctctctc cc                                                          12

<210> SEQ ID NO 12
<211> LENGTH: 12
<212> TYPE: DNA
<213> ORGANISM: Bacteriophage T7

<400> SEQUENCE: 12
gttctcgtgc cc                                                          12

<210> SEQ ID NO 13
<211> LENGTH: 12
<212> TYPE: DNA
<213> ORGANISM: Bacteriophage T7

<400> SEQUENCE: 13
atcctcgtgc cc                                                          12

<210> SEQ ID NO 14
<211> LENGTH: 12
<212> TYPE: DNA
<213> ORGANISM: Bacteriophage T7

<400> SEQUENCE: 14
gctctcgtgc cc                                                          12

<210> SEQ ID NO 15
<211> LENGTH: 12
<212> TYPE: DNA
<213> ORGANISM: Bacteriophage T7

<400> SEQUENCE: 15
gttgtggtgc cc                                                          12

<210> SEQ ID NO 16
<211> LENGTH: 79
<212> TYPE: DNA
<213> ORGANISM: Human
<220> FEATURE:
<221> NAME/KEY: gene
<222> LOCATION: (1)..(79)
<223> OTHER INFORMATION: Normal wild type CFTR oligonucleotide

<400> SEQUENCE: 16
ttatgcctgg caccattaaa gaaaatatca tctttggtgt ttcctatgat gaatatagat        60
acagaagcgt catcaaagc                                                    79

<210> SEQ ID NO 17
<211> LENGTH: 46
<212> TYPE: DNA
<213> ORGANISM: CFTR CS Probe with T7 Promoter

<400> SEQUENCE: 17
ataggaaaca ccaaagatga tattttcttt aatacgactc actata                      46

<210> SEQ ID NO 18
<211> LENGTH: 50
```

```
<212> TYPE: DNA
<213> ORGANISM: CFTR PS Probe with T7 Promoter

<400> SEQUENCE: 18
ccttgtctcc gttctggata tcacccgatg tgtctcccta tagtgagtcg          50

<210> SEQ ID NO 19
<211> LENGTH: 57
<212> TYPE: DNA
<213> ORGANISM: PSa Probe with T7 Promoter

<400> SEQUENCE: 19
tgcctccttg tctccgttct ggatatcacc cgatgtgtct ccctatagtg agtcgta   57

<210> SEQ ID NO 20
<211> LENGTH: 20
<212> TYPE: DNA
<213> ORGANISM: Synthetic Oligonucleotide Probe

<400> SEQUENCE: 20
tgcctccttg tctccgttct                                          20

<210> SEQ ID NO 21
<211> LENGTH: 25
<212> TYPE: DNA
<213> ORGANISM: Synthetic Oligonucleotide Probe

<400> SEQUENCE: 21
tccgctgcct ccttgtctcc gttct                                    25

<210> SEQ ID NO 22
<211> LENGTH: 12
<212> TYPE: DNA
<213> ORGANISM: Synthetic Oligonucleotide Probe

<400> SEQUENCE: 22
ggatatcacc cg                                                  12

<210> SEQ ID NO 23
<211> LENGTH: 47
<212> TYPE: DNA
<213> ORGANISM: CS Probe with T3 Promoter

<400> SEQUENCE: 23
ctgtatctat attcatcata ggaaacacca aattaaccct cactaaa            47

<210> SEQ ID NO 24
<211> LENGTH: 53
<212> TYPE: DNA
<213> ORGANISM: PS Probe with T3 Promoter

<400> SEQUENCE: 24
ccttgtctcc gttctggata tcacccgatg tgattccctt tagtgagggt taa     53

<210> SEQ ID NO 25
<211> LENGTH: 84
<212> TYPE: DNA
<213> ORGANISM: Hep B Oligonucleotide

<400> SEQUENCE: 25
gaggcatagc agcaggtaga agaggaagat gataaaacgc cgcagacaca tccagcgata   60
accaggacag gttggaggac agga                                         84
```

<210> SEQ ID NO 26
<211> LENGTH: 47
<212> TYPE: DNA
<213> ORGANISM: Hep B CS Probe with T3 Promoter

<400> SEQUENCE: 26
tggttatcgc tggatgtgtc tgcggcgttt tattaaccct cactaaa     47

<210> SEQ ID NO 27
<211> LENGTH: 53
<212> TYPE: DNA
<213> ORGANISM: Hep B PS Probe with T3 Promoter

<400> SEQUENCE: 27
gttctatcct gcaccgccgg agctttccac cccttccctt tagtgagggt taa     53

<210> SEQ ID NO 28
<211> LENGTH: 35
<212> TYPE: DNA
<213> ORGANISM: Streptomyces thermoalkatolerans Oligonucleotide Probe

<400> SEQUENCE: 28
cgcgatcctg caccgccgga gctttccacc ccgcg     35

<210> SEQ ID NO 29
<211> LENGTH: 45
<212> TYPE: DNA
<213> ORGANISM: CFTR CS Probe with SP6 Promoter

<400> SEQUENCE: 29
attcatcata ggaaacacca aagatgatat ttaggtgaca ctata     45

<210> SEQ ID NO 30
<211> LENGTH: 52
<212> TYPE: DNA
<213> ORGANISM: CFTR PS Probe with SP6 Promoter

<400> SEQUENCE: 30
ccttgtctcc gttctggata tcacccgatg tggtattcta tagtgtcacc ta     52

<210> SEQ ID NO 31
<211> LENGTH: 12
<212> TYPE: DNA
<213> ORGANISM: Synthetic Oligonucleotide Probe

<400> SEQUENCE: 31
ggatatcacc cg     12

<210> SEQ ID NO 32
<211> LENGTH: 120
<212> TYPE: DNA
<213> ORGANISM: Wild Type CFTR Oligonucleotide

<400> SEQUENCE: 32
gttggcatgc tttgatgacg cttctgtatc tatattcatc ataggaaaca ccaaagatga     60
tattttcttt aatggtgcca ggcataatcc aggaaaactg agaacagaat gaaattcttc    120

<210> SEQ ID NO 33
<211> LENGTH: 117
<212> TYPE: DNA
<213> ORGANISM: Mutant CFTR Oligonucleotide

<400> SEQUENCE: 33

```
gttggcatgc tttgatgacg cttctgtatc tatattcatc ataggaaaca ccaatgatat    60
tttctttaat ggtgccaggc ataatccagg aaaactgaga acagaatgaa attcttc      117
```

<210> SEQ ID NO 34
<211> LENGTH: 46
<212> TYPE: DNA
<213> ORGANISM: Mutant CFTR CS Probe with SP6 Promoter

<400> SEQUENCE: 34

```
ttatgcctgg caccattaaa gaaaatatca tttaggtgac actata              46
```

<210> SEQ ID NO 35
<211> LENGTH: 46
<212> TYPE: DNA
<213> ORGANISM: Wild Type CFTR CS Probe with T7 Promoter

<400> SEQUENCE: 35

```
cagttttcct ggattatgcc tggcaccatt aatacgactc actata              46
```

<210> SEQ ID NO 36
<211> LENGTH: 84
<212> TYPE: DNA
<213> ORGANISM: Wild Type CFTR CS Probe with T7 Promoter

<400> SEQUENCE: 36

```
ccttgtctcc gttctggata tcacccgatg tgtctcccta tagtgagtcg taagaaaata    60
tcatctttgg tgtttcctat gatg                                          84
```

<210> SEQ ID NO 37
<211> LENGTH: 17
<212> TYPE: DNA
<213> ORGANISM: Synthetic Oligionucleotide Probe

<400> SEQUENCE: 37

```
ggatatcacc cgatgtg                                                  17
```

<210> SEQ ID NO 38
<211> LENGTH: 60
<212> TYPE: DNA
<213> ORGANISM: Wild Type CFTR PS Probe with T7 and SP6 Promoter
      Sequences

<400> SEQUENCE: 38

```
gtattctata gtgtcaccta aatatttcac gcgataagta tctccctata gtgagtcgta    60
```

<210> SEQ ID NO 39
<211> LENGTH: 109
<212> TYPE: DNA
<213> ORGANISM: CFTR Oligonucleotide Probe with T3 and SP6 Promoter
      Sequence

<400> SEQUENCE: 39

```
cttcccttta gtgagggtta ataatgcctc cttgtctccg ttctcgtgga atgttgccca    60
cacctagtgc ccacgtattc tatagtgtca cctaaatatt tcacgcgat              109
```

<210> SEQ ID NO 40
<211> LENGTH: 109
<212> TYPE: DNA
<213> ORGANISM: CFTR Oligonucleotide Probe with SP6 and T3 Promoter
      Sequence

<400> SEQUENCE: 40

```
gtattctata gtgtcaccta aatatttcac gcgataagta cgtggaatgt tgcccacacc        60
tagtgcccac cttcccttta gtgagggtta ataatgcctc cttgtctcc                  109

<210> SEQ ID NO 41
<211> LENGTH: 38
<212> TYPE: DNA
<213> ORGANISM: Synthetic Probe

<400> SEQUENCE: 41
cgcgcgtgga atgttgccca cacctagtgc ccaccgcg                               38

<210> SEQ ID NO 42
<211> LENGTH: 100
<212> TYPE: RNA
<213> ORGANISM: CFTR Nucleotide Target

<400> SEQUENCE: 42
gggagaugau gacgcuucug uaucuauauu caucauagga aacaccaaag augauauuuu       60
cuuuaauggu gccaggcaua auccaggaaa acugagaaca                            100

<210> SEQ ID NO 43
<211> LENGTH: 38
<212> TYPE: RNA
<213> ORGANISM: RNA Control Sequence

<400> SEQUENCE: 43
gggagacaca ucgggugaua uccagaacgg agacaagg                               38

<210> SEQ ID NO 44
<211> LENGTH: 44
<212> TYPE: DNA
<213> ORGANISM: Ribozyme PS Probe with T7 Promoter

<400> SEQUENCE: 44
gaatctcatc agtagcgagt tctctctccc tatagtgagt cgta                        44

<210> SEQ ID NO 45
<211> LENGTH: 27
<212> TYPE: RNA
<213> ORGANISM: Human Ribozyme Substrate Probe

<400> SEQUENCE: 45
gaaucgaaac gcgaaagcgu cuagcgu                                           27
```

NUCLEIC ACID PROMOTERS

FIELD OF THE INVENTION

The present invention relates to nucleic acid hybridization probes and complexes formed therefrom, their use in nucleic acid amplification and/or nucleic acid detection processes and to kits comprising the probes and for forming said complexes. The present invention is particularly concerned with transcription and amplification of hybridized nucleic acid probes such that sensitivity of hybridization reactions is increased.

BACKGROUND OF THE INVENTION

All publications mentioned in this specification are incorporated herein by reference.

Much research has been carried out on RNA polymerases, especially bacteriophage RNA polymerases. Generally, bacteriophage RNA polymerases are exceptionally active for in vitro transcription. This high level activity may be due in part to the fact that they are composed of a single polypeptide chain and do not require a dissociating initiation factor. These polymerases have been shown to be more active on supercoiled templates although they are also very active on linear templates (Smeekens & Romano 1986 Nucl. Acids Res. 14, 2811).

Specifically, the RNA polymerase from the bacteriophage T7 has been shown to be very selective for specific promoters that are rarely encountered in DNA unrelated to T7 DNA (Chamberlin et al., 1970 Nature 228, 227; Dunn & Studier 1983 J. Mol. Biol. 166, 477). T7 RNA polymerase is able to make complete transcripts of almost any DNA that is placed under control of a T7 promoter. T7 RNA polymerase is a highly active enzyme that transcribes about five times faster than does *Escherichia coli* RNA polymerase (Studier et al, 1990 Methods Enzymol. 185, 60). The synthesis of small RNAs using T7 RNA polymerase has been described whereby sequences around the RNA polymerase promoter sequence are shown to be important in the reproducible improvement of yield of RNA produced (Milligan & Uhlenbeck, 1989 Methods Enzymol. 180, 51 and Milligan et al, 1987 Nucl. Acids Res. 15, 8783–8798). Other RNA polymerases that have similar properties to T7 include those from bacteriophage T3 and SP6, the genes for which have all been cloned and the corresponding enzymes are commercially available.

A number of nucleic acid amplification processes are disclosed in the prior art. One such process is polymerase chain reaction (PCR) disclosed in U.S. Pat. Nos. 4,683,195 and 4,683,202. The PCR amplification process, is very well-known and successful. However PCR does have drawbacks including the need for adjusting reaction temperatures alternately between intermediate (e.g. 50° C.–55° C.) and high (e.g. 90° C.–95° C.) temperatures involving repeated thermal cycling. Also, the time scale required for multiple cycles of large temperature transitions to achieve amplification of a nucleic acid sequence and the occurrence of sequence errors in the amplified copies is of the nucleic acid sequence is a major disadvantage as errors occur during multiple copying of long sequence tracts. Additionally, detection of the amplified nucleic acid sequence generally requires further processes e.g. agarose gel electrophoresis.

Alternative nucleic acid amplification processes that do utilize RNA polymerases are disclosed in WO 88/10315 (Siska Diagnostics), EP 329822 (Cangene) EP 373960 (Siska Diagnostics), U.S. Pat. No. 5,554,516 (Gen-Probe Inc.), WO 89/01050 (Burg et al), WO 88/10315 (Gingeras et al), and EP 329822 (Organon Teknika), which latter document relates to a technique known as NASBA. These amplification processes describe a cycling reaction comprising of alternate DNA and RNA synthesis. This alternate RNA/DNA synthesis is achieved principally through the annealing of oligonucleotides adjacent to a specific DNA sequence whereby these oligonucleotides comprise a transcriptional promoter. The RNA copies of the specific sequence so produced, or alternatively an input sample comprising a specific RNA sequence (U.S. Pat. No. 5,554,516), are then copied as DNA strands using a nucleic acid primer and the RNA from the resulting DNA:RNA hybrid is either removed by denaturation (WO 88/10315) or removed with RNase H (EP 329822, EP 373960 & U.S. Pat. No. 5,554,516).

The annealing of oligonucleotides forming a transcription promoter is then repeated in order to amplify RNA production. Amplification is thus achieved principally through the use of efficient RNA polymerases to produce an excess of RNA copies over DNA templates. The RNase version of this method has great advantages over PCR in that amplification can potentially be achieved at a single temperature (i.e. isothermally). Additionally, a much greater level of amplification per cycle can be achieved than for PCR i.e. a doubling of DNA copies per cycle for PCR; 10–100 RNA copies per cycle using T7 RNA polymerase.

The processes described above all refer to methods whereby a specific nucleic acid region is directly copied and these nucleic acid copies are further copied to achieve amplification. The variability between various nucleic acid sequences is such that the rates of amplification between different sequences by the same process are likely to differ, thus presenting problems for example in the quantitation of the original amount of specific nucleic acid.

The processes listed above have a number of disadvantages in the amplification of their target nucleic acid; therefore, a list of desiderata for the sensitive detection of a specific target nucleic acid sequence is outlined below;

a) the process should preferably not require copying of the target sequence, b) the process should preferably not involve multiple copying of long tracts of sequence, c) the process should preferably be generally applicable to both DNA and RNA target sequences including specific sequences without discrete ends, d) the signal should preferably result from the independent hybridization of two different probes, or regions of probe, to a target sequence, e) the process should preferably include an option for detection of hybridized probe without any additional steps.

A nucleic acid amplification process that fulfils the above desiderata is disclosed in WO 93/06240 (Cytocell Ltd). Two amplification processes are described, one thermal and one isothermal. Both the thermal and isothermal versions depend on the hybridization of two nucleic acid probes of which regions are complementary to the target nucleic acid. Portions of said probes being capable of hybridizing to the sequence of interest such that the probes are adjacent or substantially adjacent to one another, so as to enable complementary arm specific sequences of the first and second probes to become annealed to each other. Following annealing, chain extension of one of the probes is achieved by using part of the other probe as a template. Amplification of the extended probe is achieved by one of two means; in the thermal cycling version thermal separation of the extended first probe is carried out to allow hybridization of a further probe, substantially complementary to part of the newly synthesized sequence of the extended first probe. Extension of the further probe by use of an appropriate polymerase using the extended first probe as a template is achieved. Thermal separation of the extended first and further probe products provides templates for the extension of further first probe molecules and the extended first probe can act as a template for the extension of other further probe molecules.

In the isothermal version, primer extension of the first probe creates a functional RNA polymerase promoter that in the presence of a relevant RNA polymerase, allows for transcription of the probe sequence producing multiple copies of RNA. The resulting RNA is further amplified as a result of the interaction of complementary DNA oligonucleotides containing further RNA polymerase promoter sequences, whereupon annealing and extension of the RNA on the DNA oligonucleotide leads to a further round of RNA. This cyclical process generates large yields of RNA, detection of which can be achieved by a number of means.

SUMMARY OF THE INVENTION

In a first aspect the invention provides a complex comprising three strands of nucleic acid: a promoter strand, a promoter complementary strand, and a target strand; wherein the promoter complementary strand comprises the full length sequence of a first strand of a double stranded promoter; the target strand comprises a part of a second strand of the double stranded promoter; and the promoter strand comprises a part of the second strand of the double stranded promoter which is complementary to a part of the first strand; wherein neither part of the second strand of the double stranded promoter present on the target strand or on the promoter strand is capable of forming a substantially functional promoter when hybridized to the promoter complementary strand in the absence of the other part, but wherein a substantially functional promoter is formed when the promoter complementary strand is hybridized to both the target strand and the promoter strand.

The promoter strand ("PS") and the promoter complementary strand ("CS") are conveniently provided as a pair of respective "PS" and "CS" nucleic acid probes. The probes may comprise DNA, peptide nucleic acid (PNA), locked nucleic acid (LNA), (less preferably RNA) or any combination thereof.

PNA is a synthetic nucleic acid analogue in which the sugar/phosphate backbone is replaced by a peptide-linked chain (typically of repeated N-(2-aminoethyl)-glycine units), to which the bases are joined by methylene carbonyl linkages. PNA/DNA hybrids have high Tm values compared to double stranded DNA molecules, since in DNA the highly negatively-charged phosphate backbone causes electrostatic repulsion between the respective strands, whilst the backbone of PNA is uncharged. Another characteristic of PNA is that a single base mis-match is, relatively speaking, more destabilizing than a single base mis-match in heteroduplex DNA. Accordingly, PNA is useful to include in probes for use in the present invention, as the resulting probes have greater specificity than probes consisting entirely of DNA. Synthesis and uses of PNA have been disclosed by, for example, Orum et al, (1993 Nucl. Acids Res. 21, 5332); Egholm et al, (1992 J. Am. Chem. Soc. 114, 1895); and Egholm et al, (1993 Nature 365, 566).

LNA is a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. However, LNA can be synthesized on conventional nucleic acid synthesizing machines, whereas PNA cannot. Therefore, in some respects, LNA is to be preferred over PNA, for use in probes in accordance with the present invention.

The substantially functional promoter created by the formation of the complex of the invention is an RNA promoter (i.e. a structure recognized by an RNA polymerase and which causes the synthesis of RNA in the presence of a suitable polymerase and reagents). A "substantially functional" promoter may be defined for present purposes as a nucleic acid complex which possesses at least 20% or more (preferably at least 50%, more preferably at least 75%, and most preferably at least 90%) of the promoter activity of a fully double stranded, wild type promoter sequence, the relative amount of promoter activity being measured by quantitation of the amount of a given RNA transcript produced by the promoter in a given amount of time, under equivalent conditions (e.g. of temperature and ribonucleotide triphosphate concentration).

The target strand may comprise any nucleic acid (RNA or, more preferably DNA) sequence of interest, such as a sequence from a pathogen (such that the complex may be used to detect the presence of a pathogen), or may be the sequence of a particular human, animal or plant allele, such that the genotype of an individual human or animal may be determined. Conveniently (but not necessarily) at least that portion (typically 2–4 bases) of the target which contains the part of the second strand of the double stranded promoter will preferably comprise DNA. The target strand may comprise both DNA and/or RNA.

In a second aspect the invention provides a method of detecting the presence of a nucleic acid target sequence of interest, the method comprising: adding first and second probes to a sample comprising the sequence of interest, so as to form the complex of the first aspect of the invention; causing the synthesis of newly-synthesized ribonucleic acid from the substantially functional promoter present in the complex: and detecting directly or indirectly the newly-synthesized nucleic acid. The method may be used qualitatively or quantitatively. In particular, the method of the invention (and kits, as defined below) may be used for detecting the presence of single nucleotide polymorphisms ("SNP"s) in the target sequence, and may be used in high throughput screening (HTS) for pharmacogenomic investigations.

In a third aspect the invention provides a kit for forming the complex of the first aspect of the invention, the kit comprising a pair of probe molecules corresponding to the promoter strand and the promoter complementary strand, and appropriate packaging means. The kit will preferably be suitable for performing the method of the second aspect of the invention. The kit will therefore optionally comprise one or more of the following components: an RNA polymerase (particularly a T3, T7 or SP6 RNA polymerase), a DNA polymerase (particularly Klenow fragment of DNA polymerase 1, f29 polymerase, Bst polymerase and Sequenase™), deoxyribonucleotide or ribonucleotide triphosphates (labelled or unlabelled), labelling reagents and/or detection reagents (e.g. fluorophores), buffers, and instructions for use according to the method of the second aspect of the invention.

Thus, typically, the nucleic acid complex of the invention will comprise a target sequence, a CS probe, and a PS probe. The CS probe (bearing the "promoter complementary strand") comprises a target-specific region (or "foot") which hybridizes specifically to the target sequence. This target-specific region comprises the first few bases (preferably the first 2–4 bases, most preferably the first three bases) of an RNA polymerase promoter, which are hybridized with complementary bases in the target sequence. This "foot" region of the CS probe may conveniently comprise LNA and/or PNA, which increases the specificity of hybridization. Where PNA is used, all or nearly all of the target complementary region may comprise PNA. If LNA is used, it will normally suffice for 2–5 bases of the target-complementary portion to comprise LNA, the rest typically comprising conventional nucleic acid. The CS probe also comprises a non target-complementary "arm" region, which is adjacent to and contiguous with the target-specific foot region and which comprises the rest of the RNA polymerase promoter sequence.

The PS probe (bearing the "promoter strand") comprises a portion that is complementary to the "arm" region of the CS probe. The PS probe provides the rest of the sequence required to form a substantially functional RNA polymerase promoter. If desired, the PS probe may additionally comprise a target-specific "foot" region which hybridizes to the target strand in a position substantially adjacent to the CS probe, but the presence of such a target-specific region in the PS probe is not essential for performance of the invention. Where the PS probe comprises a target-complementary "foot", the foot may comprise PNA and/or LNA, as described above.

The PS probe preferably comprises a 5' template portion, which is transcribed into multiple RNA copies upon formation of the functional RNA polymerase promoter. The general principle of the invention is illustrated in FIGS. 1 and 2, and described in greater detail below. The arrangement is such that, in the absence of target nucleic acid, substantially no de novo RNA is synthesized, as no substantially functional RNA promoter is formed (the probes hybridized together, in the absence of target, being unable to provide at least 20% of the activity of the fully double stranded wild type promoter).

The present inventors are the first to appreciate that one of the strands of a double stranded RNA promoter may be discontinuous, and formed by non-ligated separate nucleic acid molecules, and yet still provide a substantially functional RNA promoter. More particularly, the inventors are the first to appreciate that this phenomenon can be utilised to provide a method of detecting the presence and/or amount of a nucleic acid sequence of interest.

The RNA polymerase promoter is preferably one recognized by a bacteriophage RNA polymerase, for example, T3, T7 or SP6 polymerase or any of the mutant forms thereof which are known to those skilled in the art. Particular mutant RNA polymerases which may be useful in performing the method of the invention are known, which may synthesize RNA or DNA (see Kostyuk et al, 1995 FEBS Letts. 369, 165–168).

The sequence of the T3 RNA polymerase promoter (described in the prior art) is:

5' AAATTMACCCTCACTAAA 3'
3' TTTMTTGGGAGTGATT 5' (Seq. ID Nos. 1 and 2)

(A number of variant T3 promoter sequences are also known, especially those in which the first three bases of the non-template strand [the upper strand shown above] are 5' TTA 3', rather than AAA.)

The sequence of the T7 RNA polymerase promoter (described in the prior art) is:

5' TAATACGACTCACTATA 3'
3' ATTATGCTGAGTGATAT 5' (Seq. ID Nos. 3 and 4)

The sequence of the SP6 RNA polymerase promoter (described in the prior art) is:

5' ATTTAGGTGACACTATA 3'
3' TAAATCCACTGTGATAT 5' (Seq. ID Nos. 5 and 6).

It is desirable that at least one of the probes in the complex comprises a "template portion" which may be used as a template by a polymerase which recognizes the promoter formed in the complex, such that the formation of the complex of the invention can allow for the synthesis of newly-synthesized ribonucleic acid, which can be detected directly or indirectly in any of a number of ways which will be apparent to those skilled in the art. The template portion is advantageously present on the promoter strand.

It will generally be preferred for the 3' end of the promoter strand to be blocked in some way, so that RNA polymerase-mediated extension thereof is not possible. This is especially desirable where the promoter strand comprises a target complementary portion. Blocking of the 3' end is conveniently accomplished by providing a phosphate group, or a propyl group, instead of an —OH group, on the 3' terminal nucleotide. Other methods of blocking the 3' end are well known to those skilled in the art.

The present inventors have found that the efficiency of initiation of RNA synthesis by the RNA polymerase promoter is affected by sequences adjacent to the promoter, downstream. In particular, a region of twelve bases (the "+12 region") is required for optimum RNA transcription. It is therefore preferred that the template portion of the complex, which is transcribed, comprises a +12 region appropriate to the polymerase which recognizes the promoter. The inventors have elucidated the optimum sequence of +12 regions for the T7 polymerase (discussed in greater detail below)—it is not known at present if these are also optimum for, say, T3 and SP6 polymerases. If, as is possible, SP6 and T3 polymerases have different optimum +12 regions, it would be a simple matter for the person skilled in the art to identify the relevant sequence by trial-and-error, with the benefit of the present disclosure.

The sequences of preferred +12 regions, for inclusion in the template portion of the promoter strand, (in respect of T7 polymerase) are shown below in Table 1. The most active +12 region (giving greatest transcription) is at the top, with the other sequences shown in decreasing order of preference.

Table 1 Alternative template +1 to +12 sequences for T7 polymerase, in descending order of transcription efficiency (Seq. ID Nos. 7–15 respectively).

5' GTTCTCTCTCCC 3'
5' GCTCTCTCTCCC 3'
5' GTTGTGTCTCCC 3'
5' GATGTGTCTCCC 3'
5' ATCCTCTCTCCC 3'
5' GTTCTCGTGCCC 3'
5' ATCCTCGTGCCC 3'
5' GCTCTCGTGCCC 3'
5' GTTGTGGTGCCC 3'

(The 5' base is numbered as +1, being the first base downstream from the end of the promoter sequence, the 3' base as +12).

In a further embodiment, the template portion of the complex (preferably on the promoter strand) could contain sequences that can be used to identify, detect or amplify the de novo synthesized RNA copies (see, for example, WO 93/06240, U.S. Pat. No. 5,554,516, or, for example, using molecular beacon sequences such as those disclosed by Tyagi & Kramer 1996 Nature Biotech 14, 303–308). These sequences are conveniently placed adjacent to, and downstream of, a +12 region (as described above) and may comprise, but are not limited to, one or more of the following: unique "molecular beacon" sequences; capture sequences; detection probe complementary sequences; alternative RNA promoter sequences for use in an isothermal amplification cycling reaction (see below). A particular unique sequence especially useful in the present invention is provided by bases 791–820 of 16S ribosomal RNA from *Streptomyces brasiliensis* (Stackebrandt et al, 1991 Appl. Environ. Microbiol. 57, 1468–1477), which sequence has no alignment with any known human DNA or DNA of a known human pathogen.

In a further embodiment of the invention it may be advantageous, when seeking to detect a sequence of interest in a mixture comprising double stranded DNA (such as genomic DNA), to include in the hybridization mixture one or more of further oligonucleotides ("blocking oligonucleotides"). These blocking oligonucleotides (preferably provided as a pair) bybridise to the sequence of interest, typically on each side of the portion which is complementary to the first probe (and the portion complementary to the second probe, if the second probe comprises a target-complementary portion). The blocking oligonucleotides preferably comprise DNA, PNA, LNA (or a combination thereof) and advantageously each comprise at least 10 (more preferably at least 20) nucleotides. The purpose of the blocking oligonucleotides is to inhibit (under the hybridization conditions employed) re-annealing of the target strand with its complementary strand. The blocking oligonucleotides may anneal to the target strand substantially adjacent to the first and second probes, or may anneal at a distance (e.g. 5–50 bases) therefrom.

Blocking oligonucleotides may offer little advantage if the first and/or second probes contain large target-complementary "feet" regions.

Detection Methods

RNA produced in accordance with the method of the invention could be detected in a number of ways, preferably following amplification (most preferably by means of an isothermal amplification step). For example, newly-synthesized RNA could be detected in a conventional manner (e.g. by gel electrophoresis), with or without incorporation of labelled bases during the synthesis.

Alternatively, for example, newly-synthesized RNA could be captured at a solid surface (e.g. on a bead, or in a microtitre plate), and the captured molecule detected by hybridization with a labelled nucleic acid probe (e.g. radiolabelled, or more preferably labelled with an enzyme, chromophore, fluorophore and the like).

One preferred detection method involves the use of molecular beacons or the techniques of fluorescence resonance energy transfer ("FRET"), delayed fluorescence energy transfer ("DEFRET") or homogeneous time-resolved fluorescence ("HTRF"). Molecular beacons are molecules which a fluorescence signal may or may not be generated, depending on the conformation of the molecule. Typically, one part of the molecule will comprise a fluorophore, and another part of the molecule will comprise a "quencher" to quench fluorescence from the fluorophore. Thus, when the conformation of the molecule is such that the fluorophore and quencher are in close proximity, the molecular beacon does not fluoresce, but when the fluorophore and the quencher are relatively widely-separated, the molecule does fluoresce. The molecular beacon conveniently comprises a nucleic acid molecule labelled with an appropriate fluorophore and quencher.

One manner in which the conformation of the molecular beacon can be altered is by hybridization to a nucleic acid, for example inducing looping out of parts of the molecular beacon. Alternatively, the molecular beacon may initially be in a hair-pin type structure (stabilised by self-complementary base-pairing), which structure is altered by hybridization, or by cleavage by an enzyme or ribozyme.

FRET (Fluorescence Resonance Energy Transfer) occurs when a fluorescent donor molecule transfers energy via a nonradiative dipole-dipole interaction to an acceptor molecule. Upon energy transfer, which depends on the $R^{-6}$ distance between the donor and acceptor, the donor's lifetime and quantum yield are reduced and the acceptor fluorescence is increased or sensitised.

The inventors have used FAM (6-carboxyfluorescein) and TAMRA (N,N,N',N'-tetramethyl-6-carboxy rhodamine) as donor and acceptor in a nucleic acid hybridization assay. The assay uses two dye labelled DNA oligomers (15 mers). FAM is linked to the 5' of one probe and TAMRA to the 3' of the other. When hybridized to target nucleic acid the probes are positioned adjacent to one another and FRET can occur. The inventors' experiments have demonstrated that for maximum signal the probes need to be spaced by five bases.

Another approach (DEFRET, Delayed Fluorescence Energy Transfer) has been to exploit the unique properties of certain metal ions (Lanthanides e.g. Europium) that can exhibit efficient long lived emission when raised to their excited states (lexcitation=337 nm, lemission=620 nm). The advantage of such long lived emission is the ability to use time resolved (TR) techniques in which measurement of the emission is started after an initial pause, so allowing all the background fluorescence and light scattering to dissipate. Cy5 (Amersham Pharmacia) (lexcitation=620 nm, lemission=665 nm) can be used as the DEFRET partner.

HTRF (see WO92/01224; U.S. Pat. No. 5,534,622) occurs where the donor (Europium) is encapsulated in a protective cage (cryptate) and attached to the 5' end of an oligomer. The acceptor molecule that has been developed for this system is a protein fluorophore, called XL665. This molecule is linked to the 3' end of a second probe. This system has been developed by Packard.

In another embodiment, the newly-synthesized RNA, before or after amplification, results in formation of a ribozyme, which can be detected by cleavage of a particular nucleic acid substrate sequence (e.g. cleavage of a fluorophore/quencher dual-labelled oligonucleotide).

Amplification Techniques

In preferred embodiments of the present invention, the RNA derived from the target dependent transcription reaction is amplified prior to detection, the amplification step typically requiring the introduction of a DNA oligonucleotide. The amplification step is advantageously effected isothermally (i.e. without requiring thermal cycling of the sort essential in performing PCR). The introduced DNA oligonucleotide is complementary to the 3' region of the newly synthesized RNA and also contains the sequence of an RNA polymerase promoter and a unique transcribable sequence (template portion). Upon hybridization of the newly-synthesized RNA with the DNA oligonucleotide, a primer extension reaction from the 3' end of the RNA, mediated by an added DNA polymerase, produces a functional double stranded RNA polymerase promoter. In the presence of the relevant RNA polymerase, multiple copies of a second RNA species are synthesized from the unique region of the DNA oligonucleotide. This RNA in turn can act as primer to a further round of primer extension and RNA synthesis. The synthesis of further RNA requires the presence of another DNA oligonucleotide that is complementary to the 3' region of the second RNA species. This DNA oligonucleotide also contains the sequence of an RNA polymerase promoter element together with a sequence upon transcription of which produces RNA comprising sequences identical to that derived in the target dependent transcription reaction. The 3' end of the RNA thus synthesized is complementary to the first DNA oligonucleotide and hence a cyclical amplification system is generated (see FIG. 3).

In these embodiments, it is important that the RNA promoter(s) formed during the amplification step(s) is (are) selected to be recognized by a polymerase different to that which recognizes the split promoter formed initially at the 2½ or 3 way junction, so as to avoid inadvertent formation of a complete promoter ab initio, which would give a very high background signal.

In a variant of the embodiment described above, the introduced DNA oligonucleotide hybridizes to the de novo synthesized RNA, the respective sequences being such that a further RNA polymerase promoter is directly formed without the need for a DNA polymerase-mediated extension step (see FIG. 13). A cycling reaction may then be performed essentially as described above, with the transcript from one reaction hybridizing with a DNA oligonucleotide to form a second RNA promoter, which produces a transcript comprising a sequence common to the original transcript.

In a further variant, an RNA species produced from a split promoter in turn comprises the first few bases of an RNA polymerase promoter, such that the RNA may in turn be the target sequence for the formation of a second split promoter (at a 2½ or 3 way junction), leading to synthesis of a further RNA species. If desired the sequences of the template portions can be selected so as to create an amplification cycle in which the RNA transcript from one split promoter forms the target for the creation of a second split promoter, which produces a transcript which re-forms the first split promoter. The scheme is illustrated schematically in FIG. 15. It will be appreciated that, in an amplification cycle of this sort, there is no requirement to use a different RNA promoter sequence to that in the original 2½ or 3 way junction, because the method would not create a fully double-stranded RNA promoter ab initio, in the absence of target.

The above system could be arranged such that an RNA transcript comprised a plurality of portions of RNA promoters, so as to be capable of forming a plurality of split promoters in a single cycle, thereby increasing the amount of amplification. Similarly, in the other types of amplification cycles described above, the added oligonucleotides could, if desired, be capable of forming a plurality of RNA promoters.

In the above amplification strategies, some background "noise" may be created because of the tendency of many RNA polymerases (at relatively low frequency) to produce RNA transcripts of a single stranded DNA sequence such that, for example, referring to FIG. 3, some transcription of DNA oligonucleotides (16) and (22) may occur even in the respective absence of RNA molecules (14) and (20); or, the same phenomenon may occur, with reference to FIG. 13, in the absence of RNA molecules (14) and (52). It is possible that this low level of background transcription can be reduced by designing the DNA oligonucleotides (16 and 22 in FIG. 3; 50 and 54 in FIG. 13) so as to incorporate near their 3' end a sequence which tends to cause termination of transcription. One example of such a sequence, which is especially effective at terminating T7 polymerase-mediated transcription, is AACAGAT (in the template strand), as disclosed by He et al, (1998 J. Biol. Chem. 273, 18,802). The same or a similar termination sequence could be positioned at the 5' end of the DNA template to increase processivity.

Various embodiments of the invention will now be described by way of illustrative examples and with reference to the accompanying drawings, in which.

Figure 1:
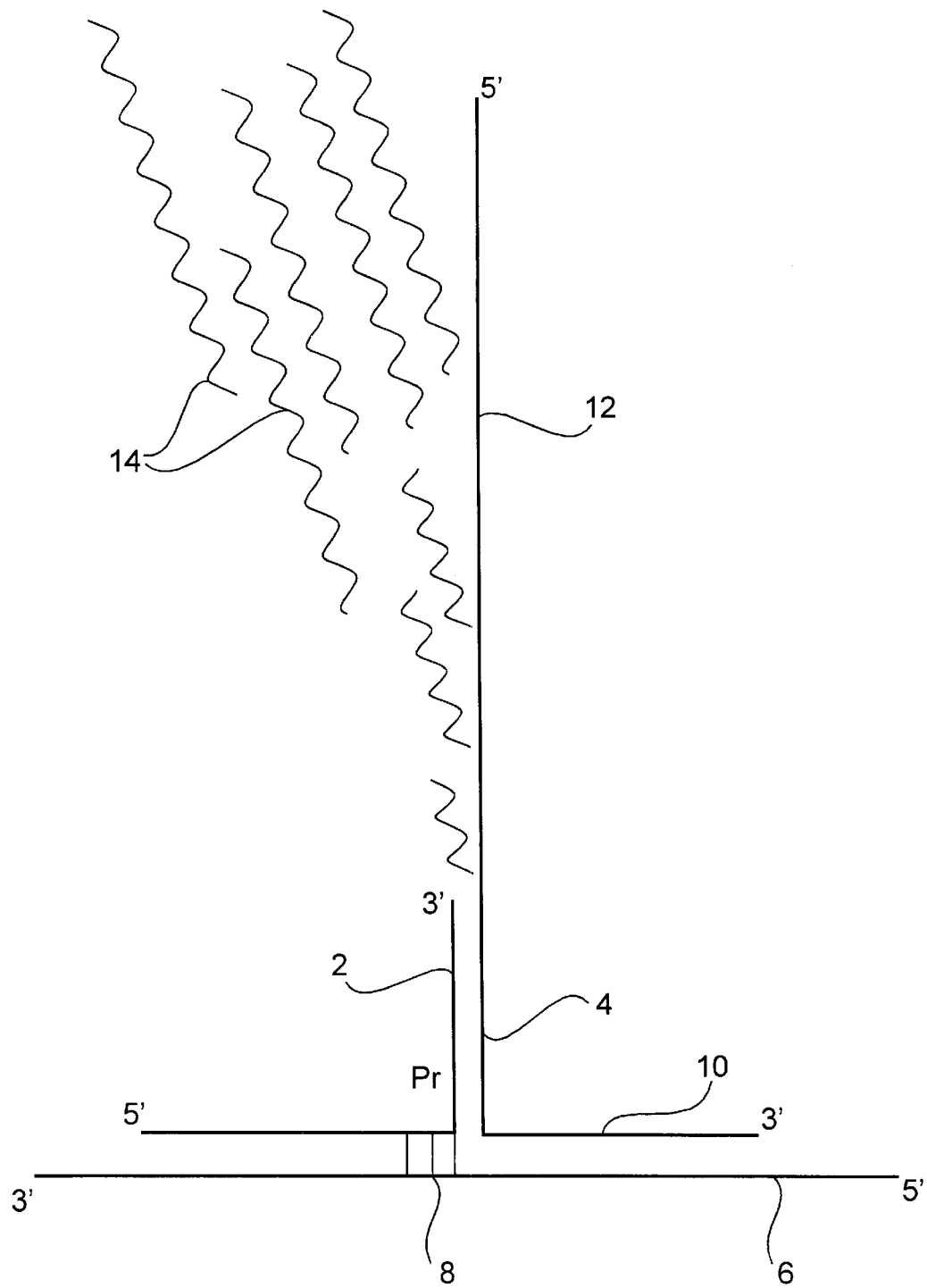
FIG. 1 is a schematic representations of a complex in accordance with the invention, comprising a "three way" junction.

FIG. 1 shows a complex in accordance with the invention. The complex comprises a promoter complementary strand "CS" (2), a promoter strand "PS" (4), and a target strand (6). The CS (2) comprises the full length sequence of a first strand of a double stranded promoter (marked "Pr" in the figure). The target strand (6) comprises three bases which are an end part (8) of a second strand of the double stranded promoter which is complementary to part of the CS (2). The PS (4) comprises the rest of the second strand of the double stranded promoter, which part is complementary to the first strand of the promoter provided on the CS (2). Hybridization of the CS (2) to the target strand (6), or hybridization of the CS (2) to the PS (4), is not sufficient to constitute a functional, double stranded promoter. However, a substantially functional promoter is formed upon hybridization of the CS (2) with both the target strand (6) and the PS (4), which represents a complex in accordance with the present invention.

In the embodiment shown in FIG. 1, the PS (4) comprises a portion (10) which is complementary to the target strand (6), such that the complex forms what may be described as a "three way junction". In an alternative embodiment, illustrated schematically in FIG. 2, the PS (4) does not comprise a portion complementary to the target strand (6), such that the complex forms what may be described as a "two-and-a-half way junction" (2½ way junction).

Figure 2:
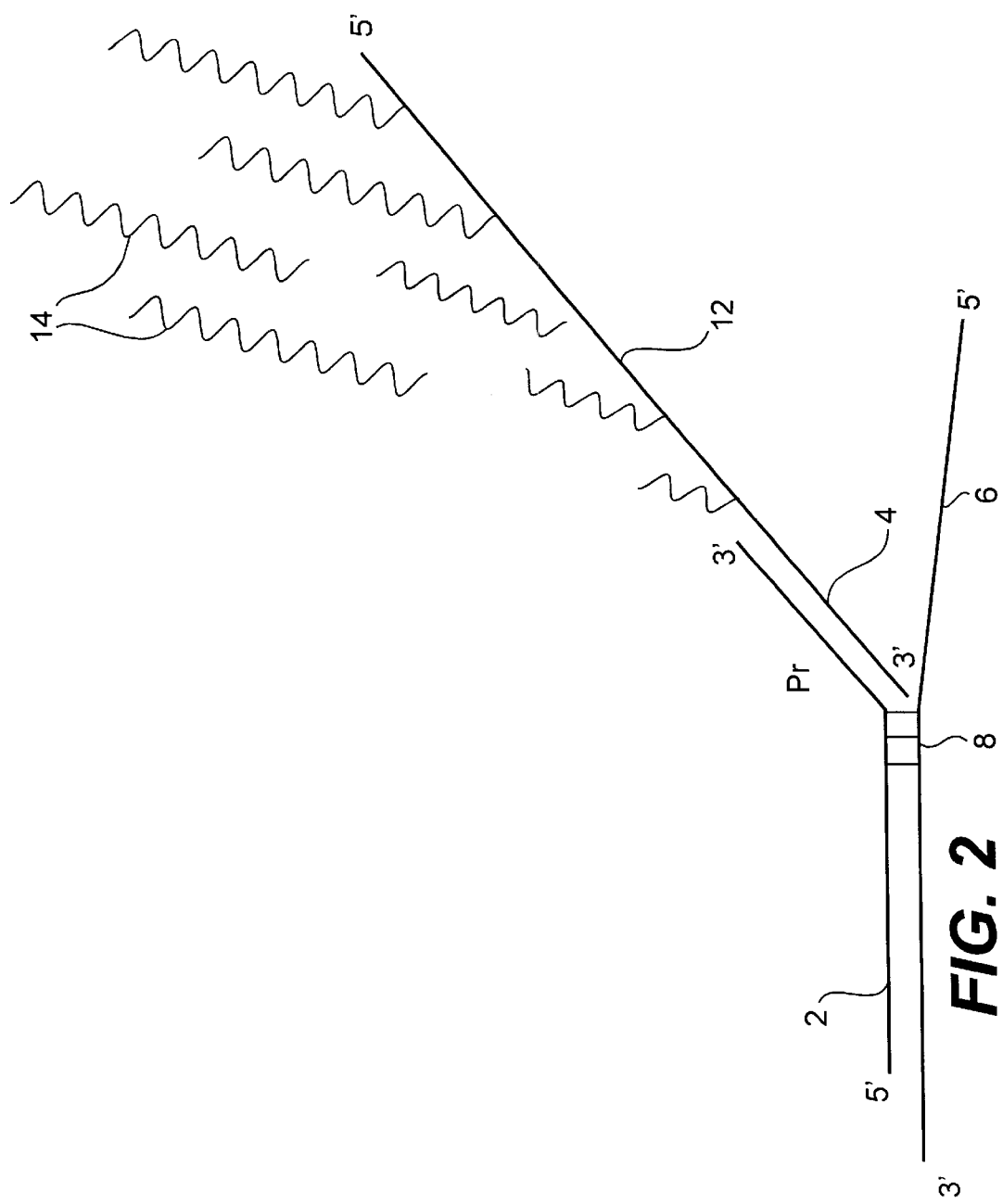
FIGS. 2, 4, 6–9, 11 and 12 are schematic representations of a complex in accordance with the invention, comprising a "2½ way" junction.

In both of the embodiments illustrated in FIGS. 1 and 2, the PS (4) comprises a template portion (12), which can act as a template nucleic acid strand for de novo nucleic acid synthesis once the functional promoter has been formed. Template portion (12) also preferably comprises a +12 region to optimize efficiency of transcription by the RNA polymerase. The newly-synthesized nucleic acid is conveniently RNA, synthesized under the influence of an RNA polymerase promoter, such that multiple RNA transcripts (14) of the template portion (12) are formed.

The de novo synthesized nucleic acid (14) may be detected directly or indirectly. Preferably the de novo synthesized nucleic acid (14) is subjected to an amplification process prior to detection. A large number of suitable detection methods will be apparent to those skilled in the art. For example, the de novo synthesized nucleic acid (14) might hybridize to a complementary oligonucleotide molecular beacon sequence (e.g. as described by Tyagi & Kramer, 1996 Nature Biotechnology 14, 303–308), such that de novo nucleic acid synthesis leads to an increase, or a decrease as appropriate, in a fluorescence signal. Alternatively, the template portion (12) may be appropriately selected such that DNA or RNA molecules synthesized with the portion (12) as a template may comprise, for example, capture sequences or detection sequences.

As mentioned above, the de novo synthesized nucleic acid is preferably subjected to an amplification step prior to detection. The amplification step is such that a small is amount of de novo synthesized nucleic acid results in the generation of a large amount of signal. Desirably, the amplification step is accomplished by performing two or more nucleic acid synthesis steps in a cyclical manner, such that the nucleic acid product of a first synthesis step acts as the primer for a second nucleic acid synthesis step, the product of which acts as the primer for the first nucleic acid synthesis step, and so on. Cycling amplification of this sort is disclosed in WO93/06240.

Figure 3:
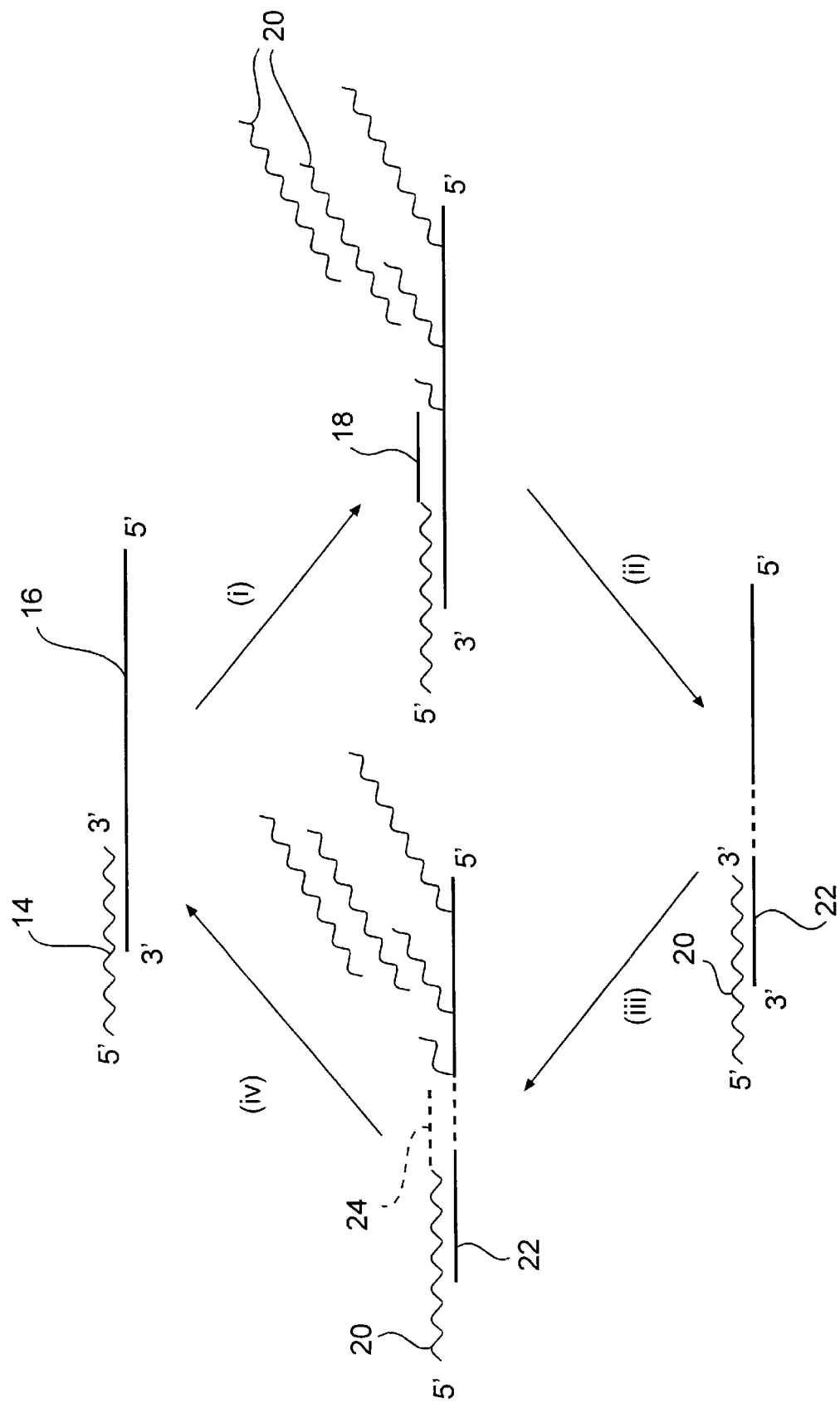
FIGS. 3, 13 and 15 are schematic representations of a method of detecting a target sequence of interest by amplifying nucleic acid synthesis.

FIG. 3 is a schematic representation of an embodiment of a cyclical nucleic acid synthesis, resulting in nucleic acid amplification. In FIG. 3, the 3' end of a de novo synthesized RNA transcript (14) produced from the template portion (12) of the second probe (4), is hybridized to an added DNA oligonucleotide (16). In step (i) the 3' end of the transcript (14) is extended by the addition of ribonucleotides and/or deoxyribonucleotides in the presence of an appropriate polymerase. In the illustrated embodiment the extended portion (of the transcript (14)) is of course complementary to the oligonucleotide (16) and forms an active double stranded RNA promoter (18) which is recognized by the appropriate RNA polymerase, so as to produce multiple copies of a second RNA species (20) which is. a transcript of the 5' end of the DNA oligonucleotide (16).

In turn, the 3' end of the RNA molecules (20) can hybridize to a further added DNA oligonucleotide (22) (step (ii)). As previously, the 3' end of the RNA molecule (20) can undergo primer extension (step iii) by the addition of ribo- or (preferably) deoxyribonucleotides, thereby forming an active double stranded RNA promoter (24), which is recognized by the relevant RNA polymerase which produces multiple copies of an RNA molecule which is a transcript of the 5' end of the DNA oligonucleotide (22).

The sequence of the DNA oligonucleotides (16) and (22) is preferably selected such that the RNA transcripts produced from the oligonucleotide (22) comprise sequences which are identical to those present in the RNA transcripts (14) produced originally, such that a cycle is formed (step iv), in which the most recently synthesized RNA molecules can hybridize to DNA oligonucleotide (16), be extended to form the RNA promoter (18) and so on. In this way, massive-amplification of the original transcript (14) may be achieved, thereby greatly enhancing the sensitivity of the detection method of the invention.

Figure 15:
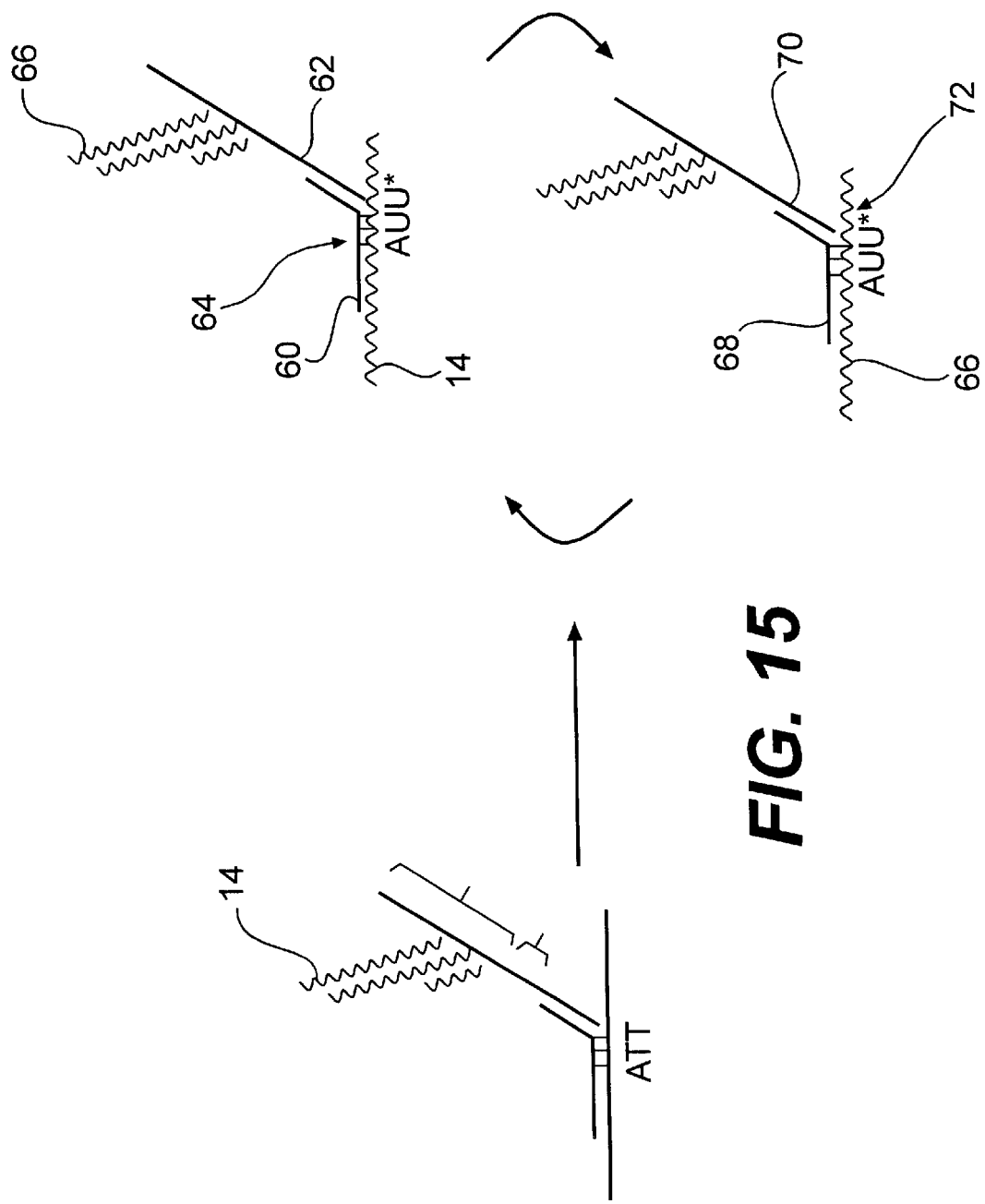

FIG. 15 is a schematic representation of an amplification cycle in which a de novo synthesized RNA transcript (14), from a split promoter formed by the presence of the sequence of interest, hybridizes to first and second probes (60, 62 respectively) to form a second split promoter (indicated generally at 64). The sequence of the template portion of second probe (62) is such that the RNA transcript (66) from split promoter (64), can act as target for a further pair of first and second probes (68, 70 respectively) creating a third split promoter (indicated generally at 2). The sequence of the template portion of the second probe (70) is such that the RNA transcript produced by split promoter (72) has substantially the same sequence as the original RNA molecule (14), so that the second split promoter (64) can be reformed, thereby creating an amplification cycle.

EXAMPLES

Example 1

Transcription from a Split T7 RNA Polymerase Promoter at a 2½ Way Junction.

This example demonstrates the creation of a functional DNA dependent RNA polymerase promoter as a result of the formation of a 2½ way junction comprising target nucleic acid (Target: wild type human DNA cystic fibrosis transmembrane conductance regulator gene (CFTR) in which a deletion of TTT causes a cystic fibrosis-encoding mutation DF508), a partly complementary oligonucleotide (complementary strand) and a promoter strand. In the example, the target sequence is provided by a synthetic oligonucleotide, which serves to demonstrate the principle of the invention. In practice, the target sequence would comprise a complex mixture of chromosomal DNA.

Figure 4:
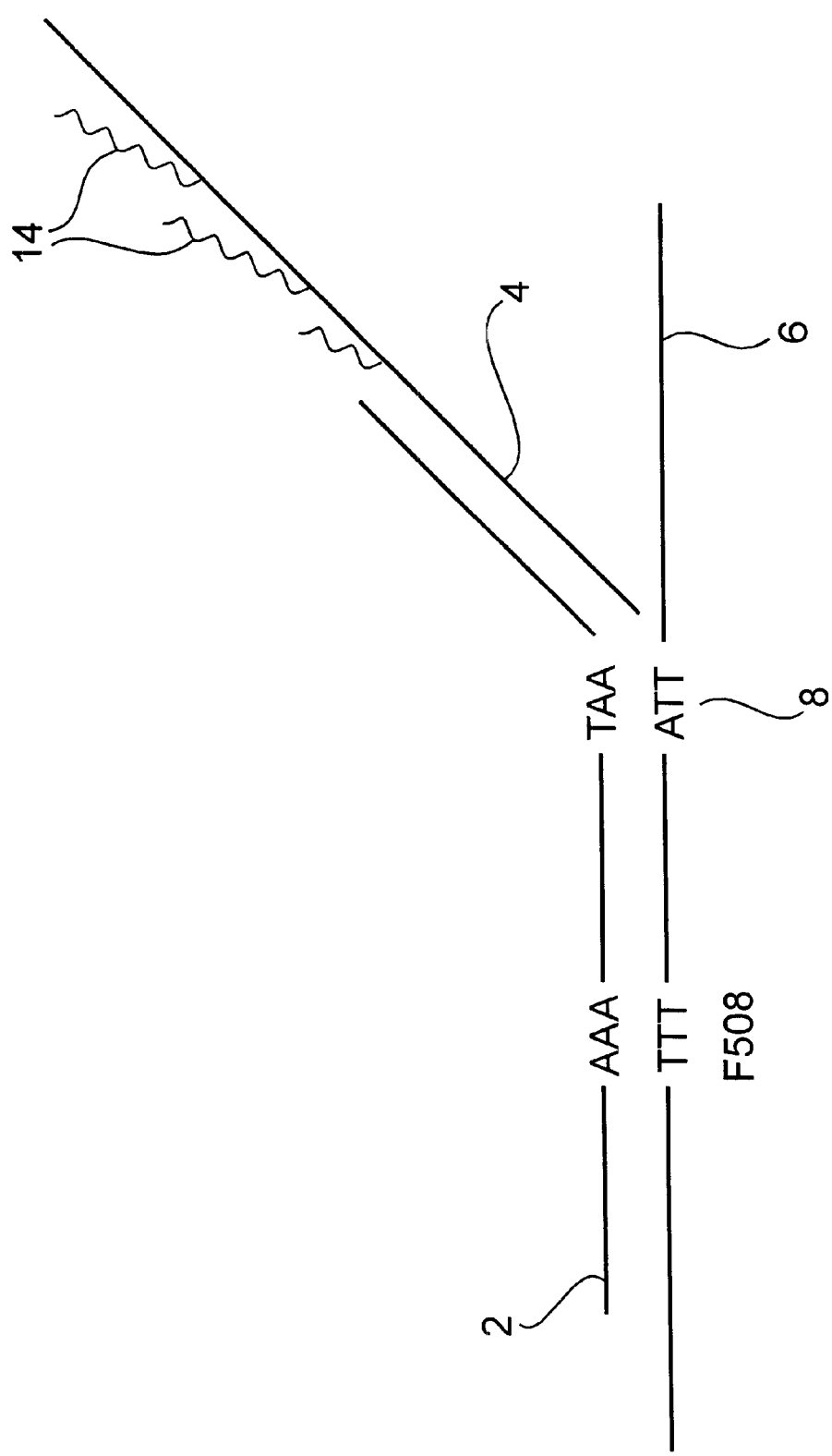

The example is illustrated schematically in FIG. 4. The complete T7 promoter is located towards the 3' end of promoter complementary strand probe (2). The first three (5') bases of the promoter sequence are complemented by three bases (3' ATT 5')(8), in target strand (6), and probe (2) hybridizes to the target (6) in such a way that the 3'TTT5' in the wild type is 14 bases downstream from the start of the promoter. Hybridization of a promoter strand probe (4), (at the 3' end of which is the complement to the T7 promoter minus three bases) to probe (2) forms a double stranded promoter, made complete by the three bases (8) in target (6), and therefore a split promoter is formed to yield a de novo synthesized RNA (14) in the presence of T7 RNA polymerase. For convenience, the promoter strand probe (4) is referred to hereafter as the PS probe, and the promoter complementary strand probe (2) is referred to hereafter as the CS probe.

1.1 Preparation of Oligonucleotides

The target oligonucleotides and probes were synthesized by phosphoramidite chemistry using an Applied Biosystems 380A synthesizer, used according to the manufacturer's instructions. All oligonucleotides were HPLC purified using standard techniques.

1.2 Split Promoter Probe and RNA Synthesis

Hybridization reactions comprised mixtures of DNA including target oligonucleotide (6), PS and CS probes, together with relevant controls comprising mixtures with and without target/probes. For hybridization reactions, 40 fmol of target oligonucleotide was mixed with 40 fmol of PS probe and 40 fmol of CS probe in a solution containing 4 $\mu$l 5×T7 RNA polymerase buffer (from Promega, giving 1× concentrations of 40 mM Tris (pH7.9), 6 mM $MgCl_2$, 2 mM spermidine and 10 mM NaCl) and distilled water to a final volume of 20 $\mu$l (following final addition of T7 RNA polymerase and rNTP mix). In this example, and others in the present specification, Milligan's buffer (Milligan et al, 1987 Nucl. Acids Res. 15, 8783–8798) may be used in place of Promega RNA polymerase buffer. Indeed, in those examples where no DNA polymerase (e.g. where there is no DNA polymerase-dependent primer extension amplification step) is used, Milligan's buffer may be preferred. The composition of Milligan's buffer is as follows: 20 mM $MgCl_2$, 5 mM DTT, 80 mg/ml PEG, 50 µg/ml BSA, 0.01% (v/v) Triton X-100, 1 mM spermidine, and 40 mM Tris HCl, pH8.1.

The mixture was heated to 90° C. for 3 minutes to denature the nucleic acids, incubated on ice for 2 minutes, and equilibrated to 37° C. for 1 minute. Probes were annealed and transcribed at 37° C. for 180 minutes by addition of 40 units of T7 RNA polymerase (Promega) and 40 nmoles rNTP mix (Pharmacia Biotech). DNA oligonucleotides were removed from the reaction mix by the addition of 4 units of DNase I (Ambion) and incubating at 37° C. for 20 minutes prior to end detection. The resulting product was immobilised by hybridization to a specific biotinylated oligonucleotide (probe 3) which was in turn bound to a streptavidin coated well. The immobilised product was detected by time resolved fluorescence via the hybridization of probe 4, a europium labelled oligonucleotide probe (see below).

1.3 Detection of RNA by Time Resolved Fluorescence (TRF)

Figure 5:
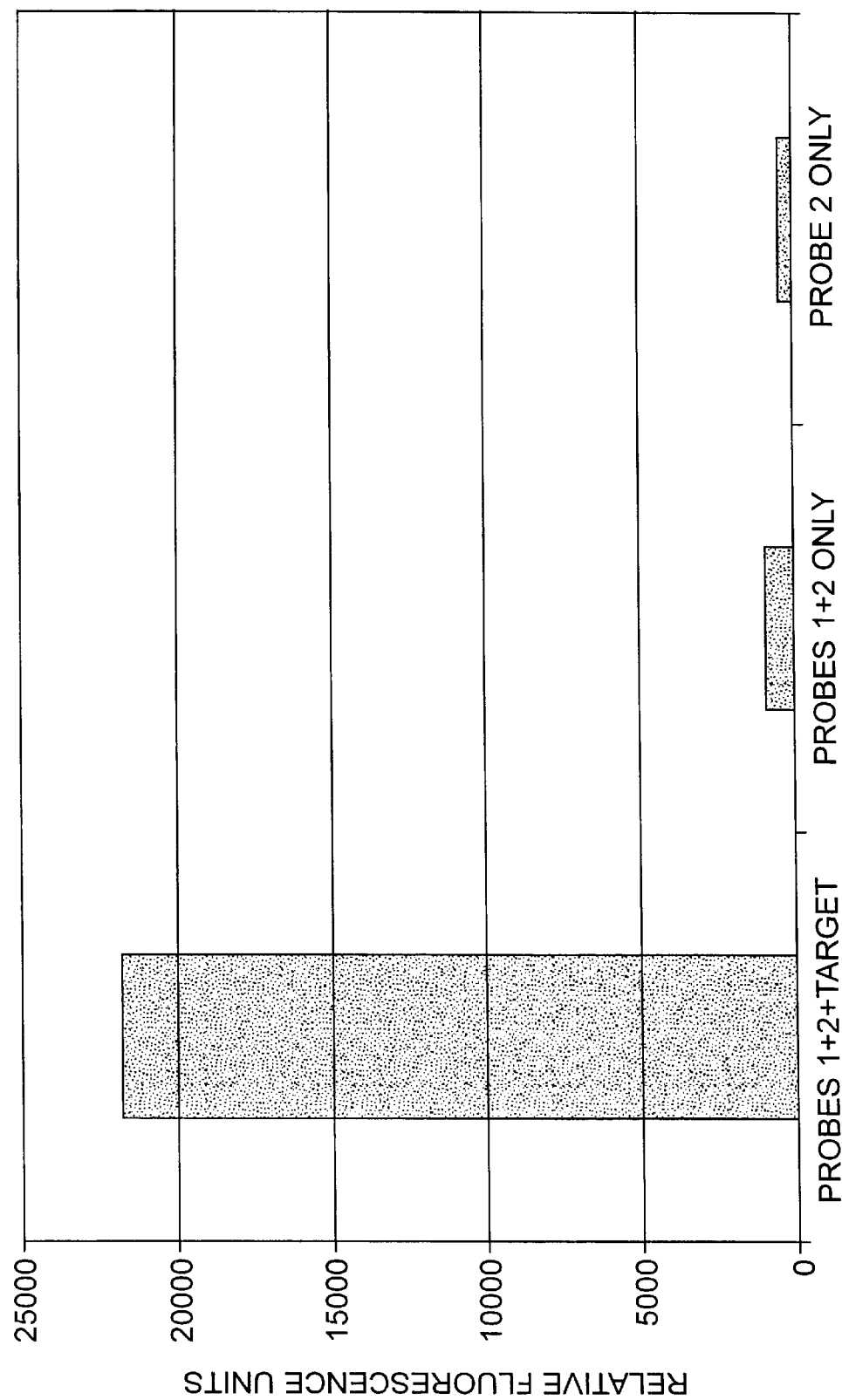
FIG. 5 is a bar chart showing relative fluorescence units present following various nucleic acid amplification reactions.

5 µl of reaction sample was added to the reaction mix consisting of 145 µl of Wallac (E.G. & G. Wallac, Crown Hill Business Centre, Milton Keynes, UK) assay buffer, 0.9 pmol of probe 3 and 0.3 pmol of probe 4 in a well of a Labsystems streptavidin coated microtitre plate, which was incubated at room temperature for 60 minutes (N.B. the use of longer probe PS gives a transcript with a longer capture tail, so that capture of this with the extended biotinylated probe 3a results in more sensitive detection). Unbound material was removed by washing the wells 4× with 200 µl of Wallac wash solution. 180 µl of Wallac enhancement solution was added to dissociate the europium from its chelated bonding to probe 4, and TRF was measured every 10 minutes up to 60 minutes using the europium protocol on a Wallac Victor 1420 Multilabel Counter. The results obtained (using Probes PSa and 3a) are shown in FIG. 5.

1.4 List of Oligonucleotides

In general, in the oligonucleotide sequences disclosed in Example 1 and the successive examples below: lower case letters denote the site of the DF508 mutation; promoter portions are shown underlined; portions of probes used for detection purposes are indicated by italics; and capture portions are shown in bold face. The 3' phosphate groups on PS probes (where included) are optional.

Target oligonucleotide (Normal wild type CFTR DNA)
5' TTATGCCTGGCACCA TTAAGAAAATATCATCtttGGTGTTTCCTATGATGA ATATAGATACAGAAGCGTCATCAAAGC 3' (Seq. ID No. 16)

CS probe (T7 promoter)
5' ATAGGAAACACCAAAGATGATATTTTCTT TAATACGACTCACTATA 3' (Seq. ID No. 17)

PS probe (T7 promoter with 3' ATT 5' start sequence in target, and template portion)
5' CCTTGTCTCCGTTCTGGATATCAC-CCGATGTGTCTCCC*TATAGTGAGTCGTA* 3' (Seq. ID No.18)

PSa probe (T7 promoter with 3' ATT 5' start sequence in target, and template portion with capture tail extended to 20 bases for more sensitive capture and detection, using probe 3*a*)
5' TGCCTCCTTGTCTCCGTTCTGGATAT-CACCCGATGTGTCTCCC*TATAGTGAGTCGTA* phosphate 3' (Seq. ID No. 19)

Probe 3 (with 5' biotin to allow capture on streptavidin coated plates)
5' TGCCTCCTTGTCTCCGTTCT 3' (Seq. ID No. 20)

Probe 3a (version of probe 3a extended by 5 bases to allow more sensitive capture of transcript from probe PSa)
5' TCCGCTGCCTCCTTGTCTCCGTTCT 3' (Seq. ID No. 21)

Probe 4 (europium-labelled)
5' *GGATATCACCCG* 3' (Seq. ID No. 22)

Example 2

Transcription from a Split T3 RNA Polymerase Promoter at a 2½ Way Junction at DF508

Figure 6:
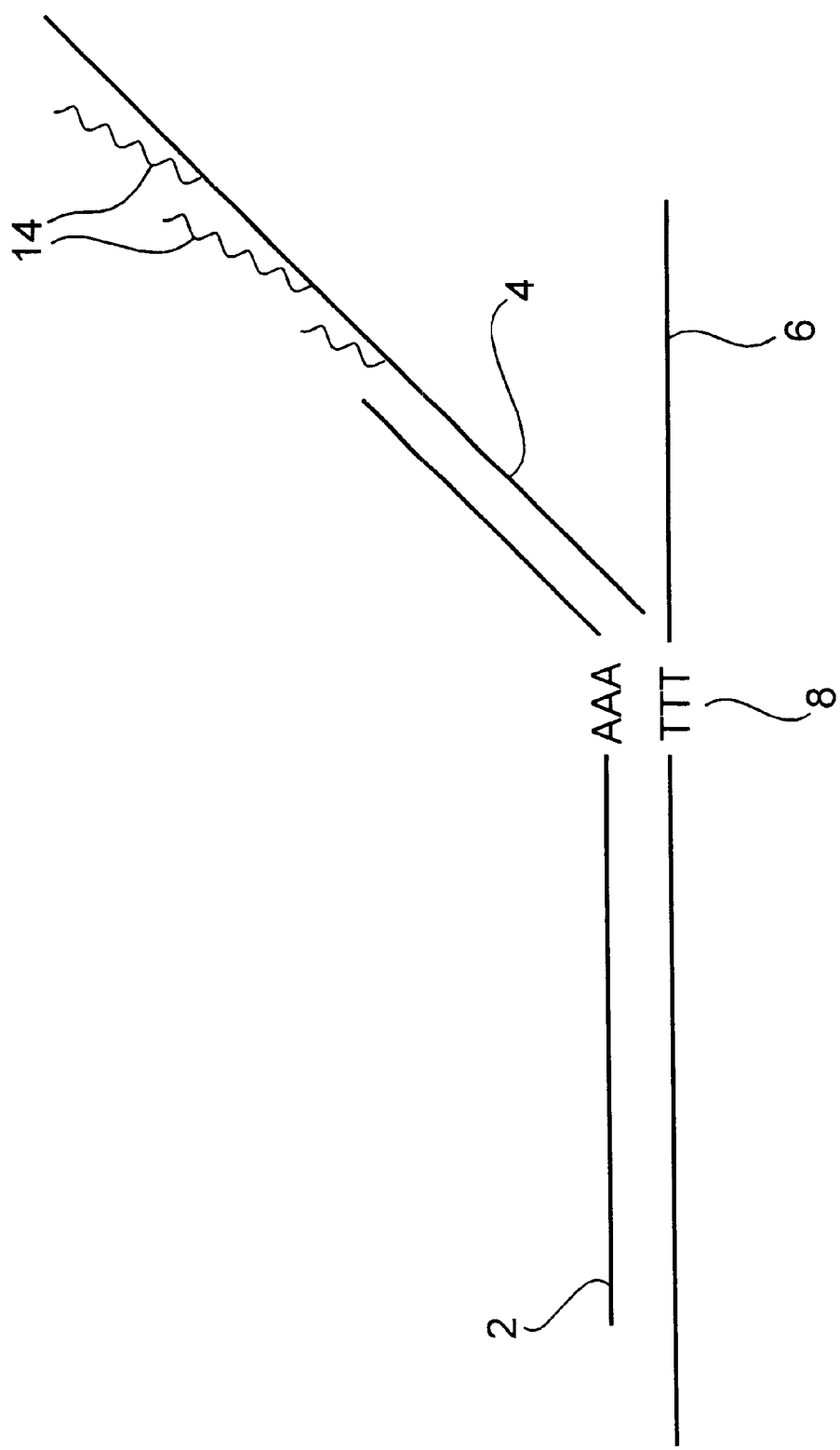

The example is illustrated schematically in FIG. 6. The complete T3 promoter is located towards the 3' end of the CS probe (2). The first three bases of the T3 RNA polymerase promoter (5' AAA3') in the CS probe (2) anneals to the 3' TTT5' DF508 site (8) in the wild type target (6), and therefore the DF508 mutation will result in loss of the split promoter start, with subsequent loss of transcription. Hybridization of a PS probe (4), (at the 3' end of which is the complement to the T3 promoter minus three bases) to CS probe (2) forms a double stranded promoter, made complete by the three bases (3' TTT 5') in the target, and therefore a split promoter is formed to yield a de novo synthesized RNA (14) in the presence of T3 RNA polymerase.

2.1 Preparation of Oligonucleotides

The target oligonucleotides and probes are synthesized and purified as described in Example 1.

2.2 Split Promoter Probe and RNA Synthesis

Hybridization reactions comprise mixtures of DNA including target oligonucleotide, PS and CS probes, together with relevant controls comprising mixtures with and without target/probes PS and CS. Hybridization reactions are established as described in Example 1.2, but using the probe sequences detailed below and T3 RNA polymerase/buffer (Promega). The hybridization mixture is then treated as described in Example 1, but using probe 3 and probe 4 sequences detailed below.

2.3 Detection of RNA by Time Resolved Fluorescence (TRF)

5 µl of reaction sample is added to the reaction mix consisting of 145 µl of Wallac assay buffer, 0.9 pmol of probe 3 and 0.3 pmol of probe 4 in a well of a Labsystems streptavidin coated microtitre plate, which is incubated at room temperature for 60 minutes. The assay is then performed as described above (at Example 1.3).

2.4 List of Oligonucleotides

Target oligonucleotide (Normal wild type DNA)
5' TTATGCCTGGCACCATTAAAGAAAATATCATC tttGGTGTTTCCTATGATGA ATATAGATACA-GAAGCGTCATCAAAGC 3' (Seq. ID No. 16)

CS Probe (T3 promoter) (Seq. ID No. 23)
5° CTGTATCTATATTCATCATAGGAAACAC-CAAATTAACCCTCACTAAA3'

PS Probe (T3 promoter with 3' TTT 5' start sequence in target, and template portion)
5° CCTTGTCTCCGTTCTGGATATCAC-CCGATGTGATTCCC*TTTAGTGAGGGTTAA* phosphate 3' (Seq. ID No. 24)

Probe 3 (with 5' biotin to allow capture on streptavidin coated plates)
5' TGCCTCCTTGTCTCCGTTCT 3' (Seq. ID No. 20)

Probe 4 (europium-labelled)
5' *GGATATCACCCG* 3' (Seq. ID. No. 22)

Example 3

Transcription from a Split T3 RNA Polymerase Promoter at a 2½ Way Junction

Figure 7:
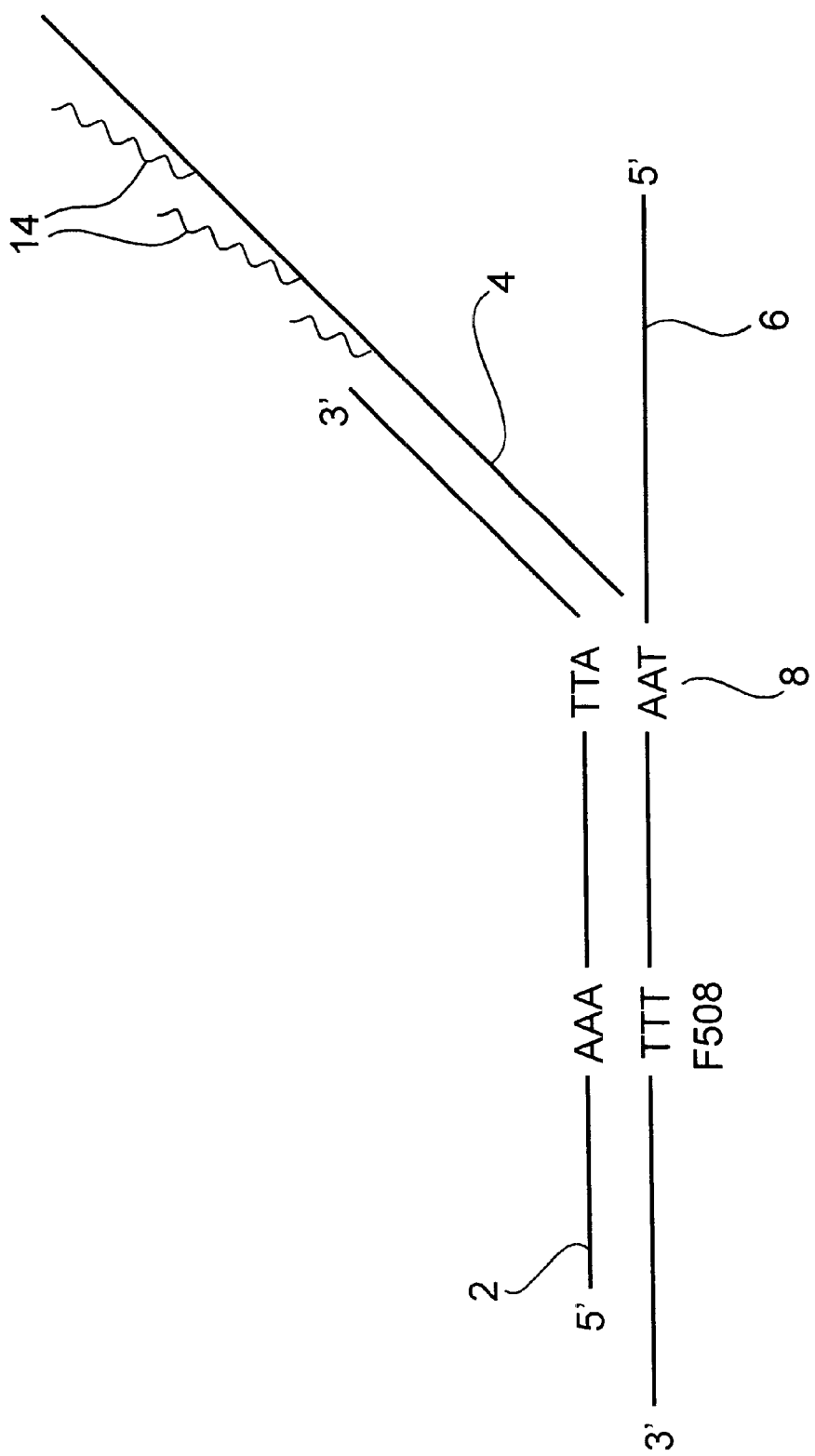

The example is illustrated schematically in FIG. 7. The complete T3 promoter (the first three bases of which is 5' TTA 3', a different version to that in example 2) is located towards the 3' end of the CS probe (2). The first three (5') bases of the promoter sequence is complemented by three bases (3' AAT 5'), (8) in the target (6) (Target: Hepatitis B (Hep B) DNA). Hybridization of a PS probe (4), (at the 3' end of which is the complement to the T3 promoter minus three bases) to CS probe (2) forms a double stranded promoter, made complete by the three bases (3' AAT 5') in the target (6), and therefore a split promoter is formed to yield a de novo synthesized RNA in the presence of T3 RNA polymerase.

3.1 Preparation of Oligonucleotides

The target oligonucleotides and probes were synthesized and purified as described in Example 1.

3.2 Split Promoter Probe and RNA Synthesis

Hybridization reactions are established as described in Example 2.2 and treated as described in Example 1.2 above, but using the nucleic acid sequences detailed below. The resulting product is detected by the hybridization of molecular beacon (see below).

3.3 Detection of RNA by Molecular Beacon Assay

5 µl of reaction sample is added to the reaction mix consisting of 145 µl of hybridization solution and 2 pmol molecular beacon (fluorophore=FAM; quencher=methyl red), in a Labsystems White Microstrip microtitre plate, which is incubated in the dark at room temperature for 60 minutes. Fluorescence signal from the hybridized beacon/target is measured using the Wallac Victor 1420 Multilabel Counter, using the fluorescein protocol.

3.4 List of Oligonucleotides

Target (Hep B DNA)

5' GAGGCATAGCAGCAGGATGAAGAGGAA-GATGA<u>TAA</u>AACGCCGCAGACACA TCCAGC-GATAACCCAGGACAGGTTGGAGGACAGGA 3' (Seq. ID No. 25)

CS Probe (T3 promoter)

5' TGGTTATCGCTGGATGTGTCTGCGGCGTT TTAT<u>TMCCCTCACTAAA</u> 3' (Seq. ID No. 26)

PS Probe (T3 promoter with 3' AAT 5' start sequence in target, and template portion)

Figure 8:
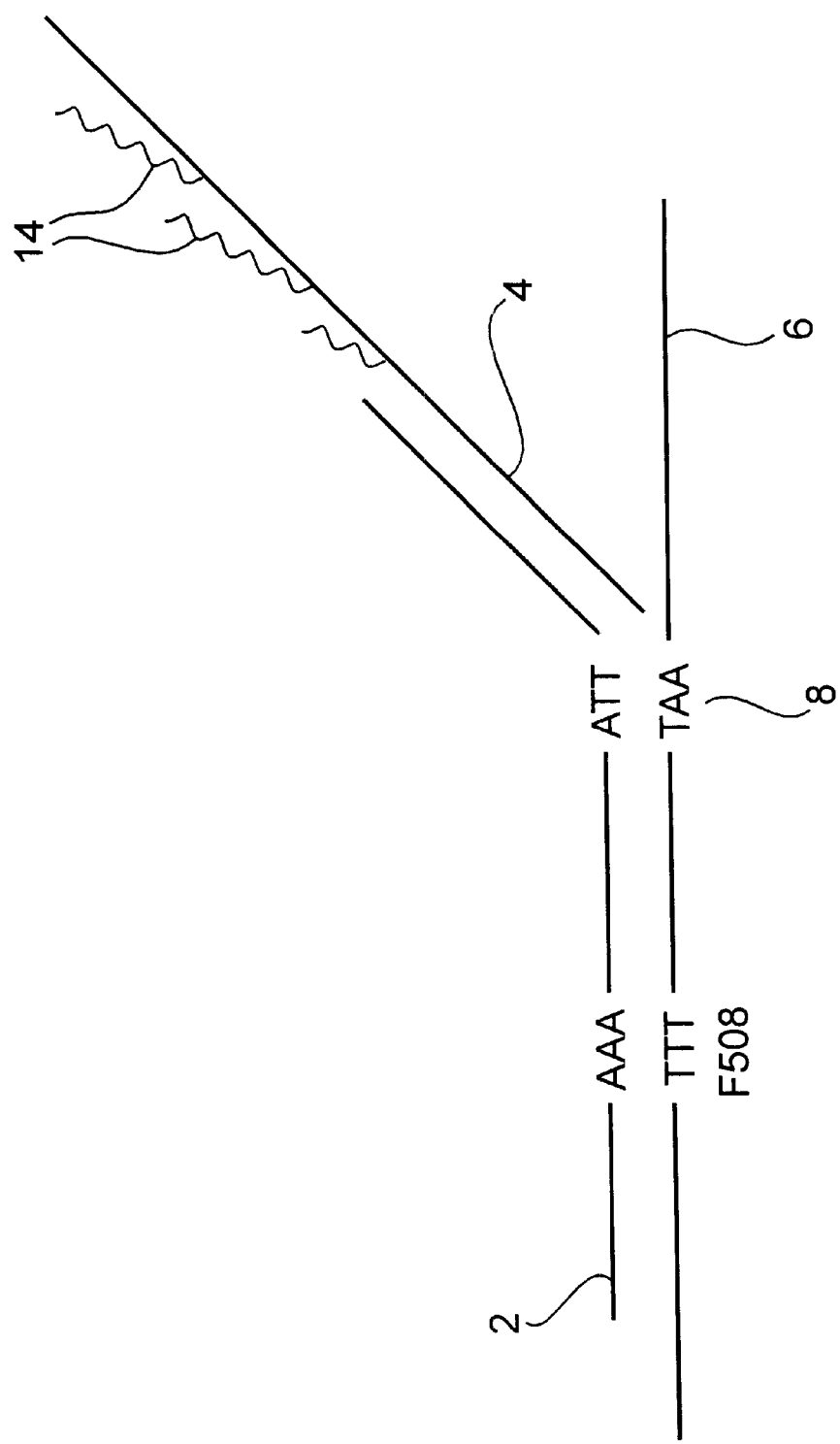

The example is illustrated schematically in FIG. 8. The complete SP6 promoter is located towards the 3' end of the CS probe (2). The first three (5') bases of the promoter sequence is complemented by three bases (3' TAA 5') (8) in the target (6), and the CS probe (2) hybridizes to the target (6) in such a way that the 3' TTT 5' in the wild type is 6 bases downstream from the start of the promoter. Hybridization of a PS probe (4), (at the 3' end of which is the complement to the SP6 promoter minus three bases) to CS probe (2) forms a double stranded promoter, made complete by the three bases (3' TAA 5') in the target, and therefore a split promoter is formed to yield a de novo synthesized RNA (14) in the presence of SP6 RNA polymerase.

4.1 Preparation of Oligonucleotides

The target oligonucleotides and probes are synthesized and purified as described in Example 1.

4.2 Split Promoter Probe and RNA Synthesis

Hybridization reactions are established and treated as described in Example 1.2, but using the nucleic acid sequences detailed below and using SP6 RNA polymerase/buffer (Promega).

4.3 Detection of RNA by Time Resolved Fluorescence (TRF)

5 µl of reaction sample is added to the reaction mix consisting of 145 µl of Wallac assay buffer, 0.9 pmol of probe 3 and 0.3 pmol of probe 4 in a well of a Labsystems streptavidin coated microtitre plate, which is incubated at room temperature for 60 minutes. The assay is then performed as described above (at section 1.3).

4.4 List of Oligonucleotides

Target oligonucleotide (Normal wild type DNA)

5' TTATGCCTGGCACCATTAAAGAA <u>AAT</u>ATCATC<u>ttt</u>GGTGTTTCCTATGATGA ATATA-GATACAGAAGCGTCATCAAAGC 3' (Seq. ID No. 16)

CS Probe (SP6 promoter)

5' ATTCATCATAGGAAACACCAAAGATGAT AT<u>TTAGGTGACACTATA</u> 3' (Seq. ID No. 29)

PS Probe (SP6 promoter with 3' TAA5' start sequence in target, and template portion)

5' CCTTGTCTCCGTTCTGGATATCAC-CCGATGTGGTATTC<u>TATAGTGTCACCTA</u> phosphate 3' (Seq. ID No. 30)

Probe 3 (with 5' biotin to allow capture on streptavidin coated plates)

5' TGCCTCCTTGTCTCCGTTCT 3' (Seq. ID No. 20)

Probe 4 (europium-labelled)

```
        molecular beacon sequence
5' GTTCTATCCTGCACCGCCGGAGCTTTCCACCCCTTCCCTTTAGTGAGGGTTA  (Seq. ID No. 27)

A phosphate 3'
```

Molecular Beacon Oligonucleotide probe (comprising a sequence derived from *Streptomyces thermoalkatolerans*, with complementary 5' and 3' ends)

5' CGCGATCCTGCACCGCCGGAGCTTTC-CACCCCGCG 3' (Seq. ID No. 28)

Example 4

Transcription from a Split SP6 Promoter at a 2½ Way Junction

In this example, the target is wild type human DNA CFTR gene in which a deletion of TTT causes a cystic fibrosis-encoding mutation DF508.

5' GGATATCACCCG 3' (Seq. ID No. 31)

Example 5

Transcription from a Split SP6 RNA Polymerase Promoter at a 2½ Way Junction at DF508

Figure 9A:
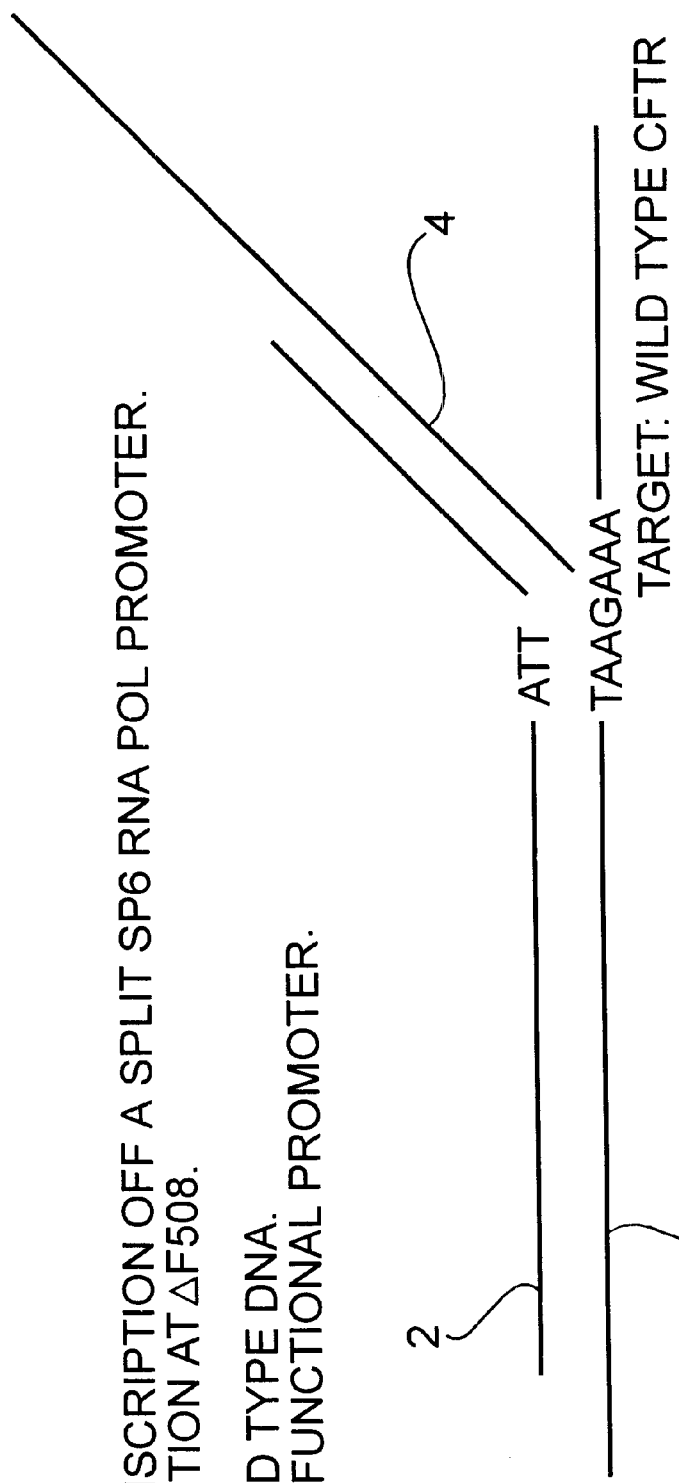
Figure 9B:
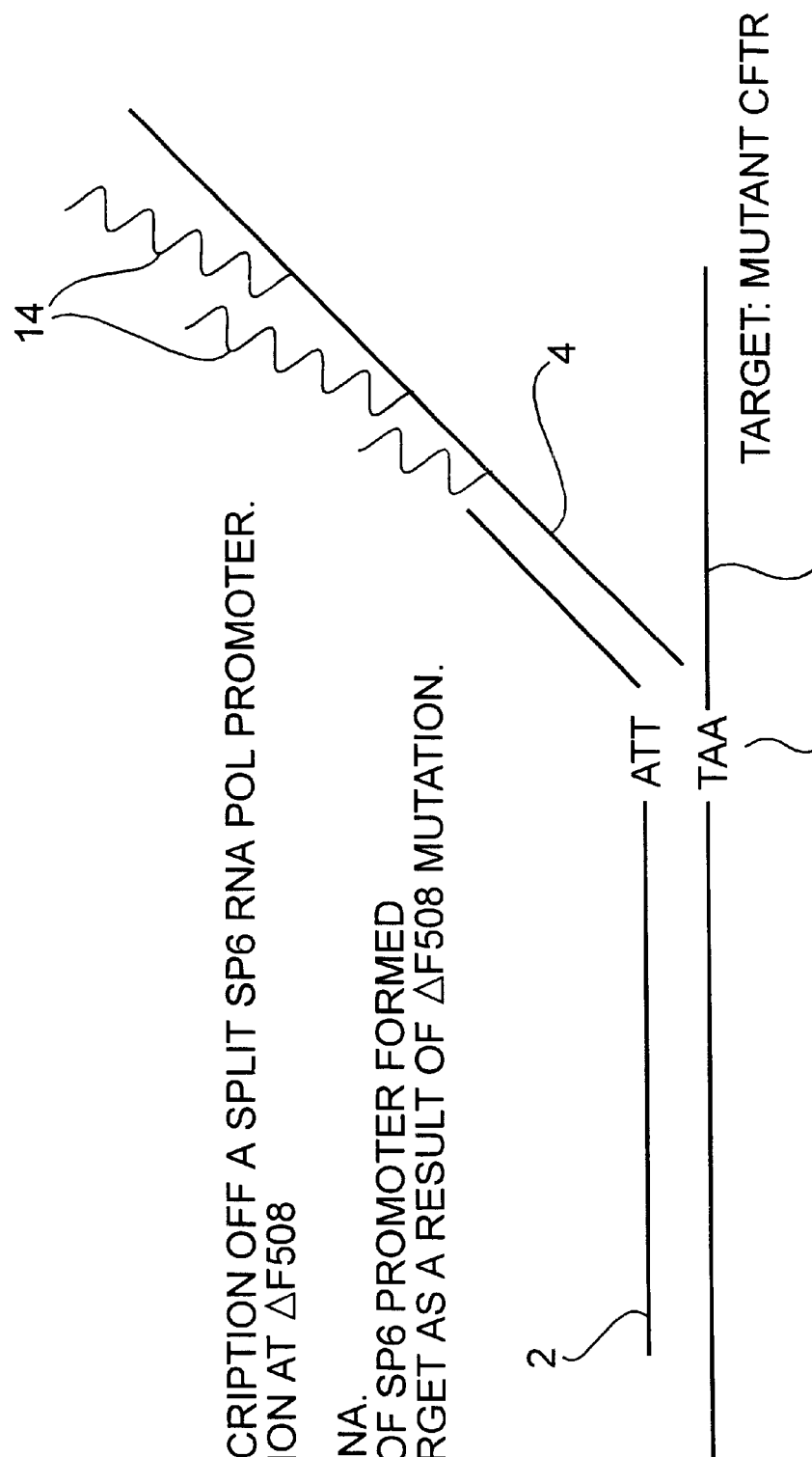

The example is illustrated schematically in FIGS. 9A and 9B. One conformation of the DF508 CFTR mutation results in the loss of a 3' GAA 5' from the sequence 3' TAGAAA 5', resulting in the creation of a 3' TAA 5' triplet (8) and thus an SP6 promoter start sequence (FIG. 9B). Hence a functional SP6 promoter is created using CS probe (2) and PS probe (4) with CFTR mutant DNA target (6), whereas no functional promoter is created using PS and CS probes with normal wild type DNA target (FIG. 9A). Hybridization of a PS probe (4), (at the 3' end of which is the complement to the SP6 promoter minus three bases) to CS probe (2) forms a double stranded promoter, made complete by the three bases (3' TAA 5') in the mutant target (6), and therefore a split promoter is formed to yield a de novo synthesized RNA in the presence of SP6 RNA polymerase.

5.1 Preparation of Oligonucleotides

The target oligonucleotides and probes are synthesized and purified as described in Example 1.

5.2 Split Promoter Probe and RNA Synthesis

Hybridization reactions are established and treated as described in Example 1.2, but using the nucleic acid sequences detailed below and using SP6 RNA polymerase/ buffer (Promega).

5.3 Detection of RNA by Time Resolved Fluorescence (TRF)

5 µl of reaction sample is added to the reaction mix consisting of 145 µl of Wallac assay buffer, 0.9 pmol of probe 3 and 0.3 pmol of probe 4 in a well of a Labsystems streptavidin coated microtitre plate, which is incubated at room temperature for 60 minutes. The assay is then performed as described above (section 1.3).

5.4 List of Oligonucleotides

Target oligonucleotide (Normal wild type DNA, no DF508 deletion)

5' GTTGGCATGCTTTGATGACGCTTCTG-TATCTATATTCATCATAGGAAACACC AaagAT-GATATTTTCTTTAATGGTGCCAGGCAT-AATCCAGGAAAACTGAGAACAG AATGAAATTCTTC 3' (Seq. ID No. 32)

Target oligonucleotide (CF mutant DNA, with the DF508 deletion)

5' GTTGGCATGCTTTGATGACGCTTCTG-TATCTATATTCATCATAGGAAACACC aatGATATTTTCTTTAATGGTGCCAGGCATAATC CAGGAAAACTGAGAACAGAATG AAATTCTTC 3' (Seq. ID No. 33)

CS Probe (SP6 promoter)

5' TTATGCCTGGCACCATTAAAGAAAATATC ATTTAGGTGACACTATA 3' (Seq. ID No. 34)

PS Probe (SP6 promoter with 3' TAA 5' start sequence formed by a DF508 mutation in CFTR mutant DNA, and template portion)

5° CCTTGTCTCCGTTCTGGATATCAC-CCGATGTGGTATTCTATAGTGTCACCTA phosphate 3' (Seq. ID No. 30)

Probe 3 (with 5' biotin to allow capture on streptavidin coated plates)

5' TGCCTCCTTGTCTCCGTTCT 3' (Seq. ID No. 20)

Probe 4 (europium-labelled)

5' GGATATCACCCG 3' (Seq. ID No. 22)

Example 6

Transcription from a Split T7 RNA Polymerase Promoter at a 3 Way Junction

In this example, the target is wild type human DNA CFTR gene, at which a deletion of TTT causes a cystic fibrosis-encoding mutation DF508.

The complete T7 promoter is located towards the 3' end of a CS probe. The first three (5') bases of this sequence complement three bases in the target. Hybridization of a PS probe, (which has the complement to the T7 promoter minus three bases, and a complement to the target DNA) to CS probe and the target forms a double stranded promoter, made complete by the three bases in the target, and therefore a split promoter is formed to yield a de novo synthesized RNA in the presence of T7 RNA polymerase.

6.1 Preparation of Oligonucleotides

The target oligonucleotide and probes were synthesized and purified as described in Example 1.

6.2 Split Promoter Probe and RNA Synthesis

Hybridization reactions were established and treated as described in Example 1.2, but using the nucleic acid sequences detailed below. The resulting product was immobilised by hybridization to a specific biotinylated oligonucleotide (probe 3) which was in turn bound to a streptavidin coated well of a microtitre plate. The immobilised product was detected by colorimetry via the hybridization of probe 4, an alkaline phosphatase-labelled oligonucleotide probe (see below).

6.3 Detection of RNA by Colorimetry

Figure 10:
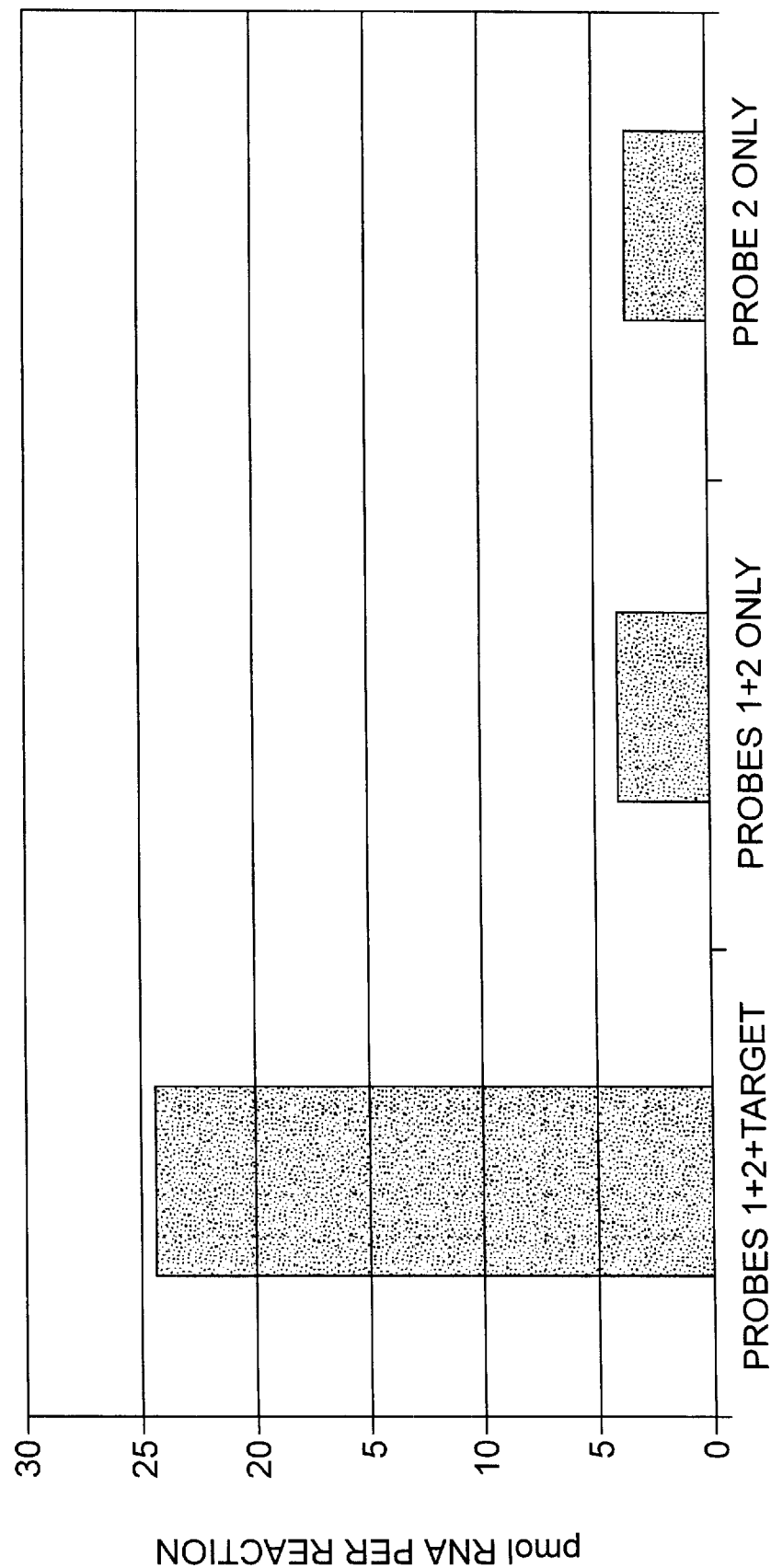
FIGS. 10 and 14 are bar charts showing picomoles of RNA produced following various nucleic acid amplification reactions.
Figure 11:
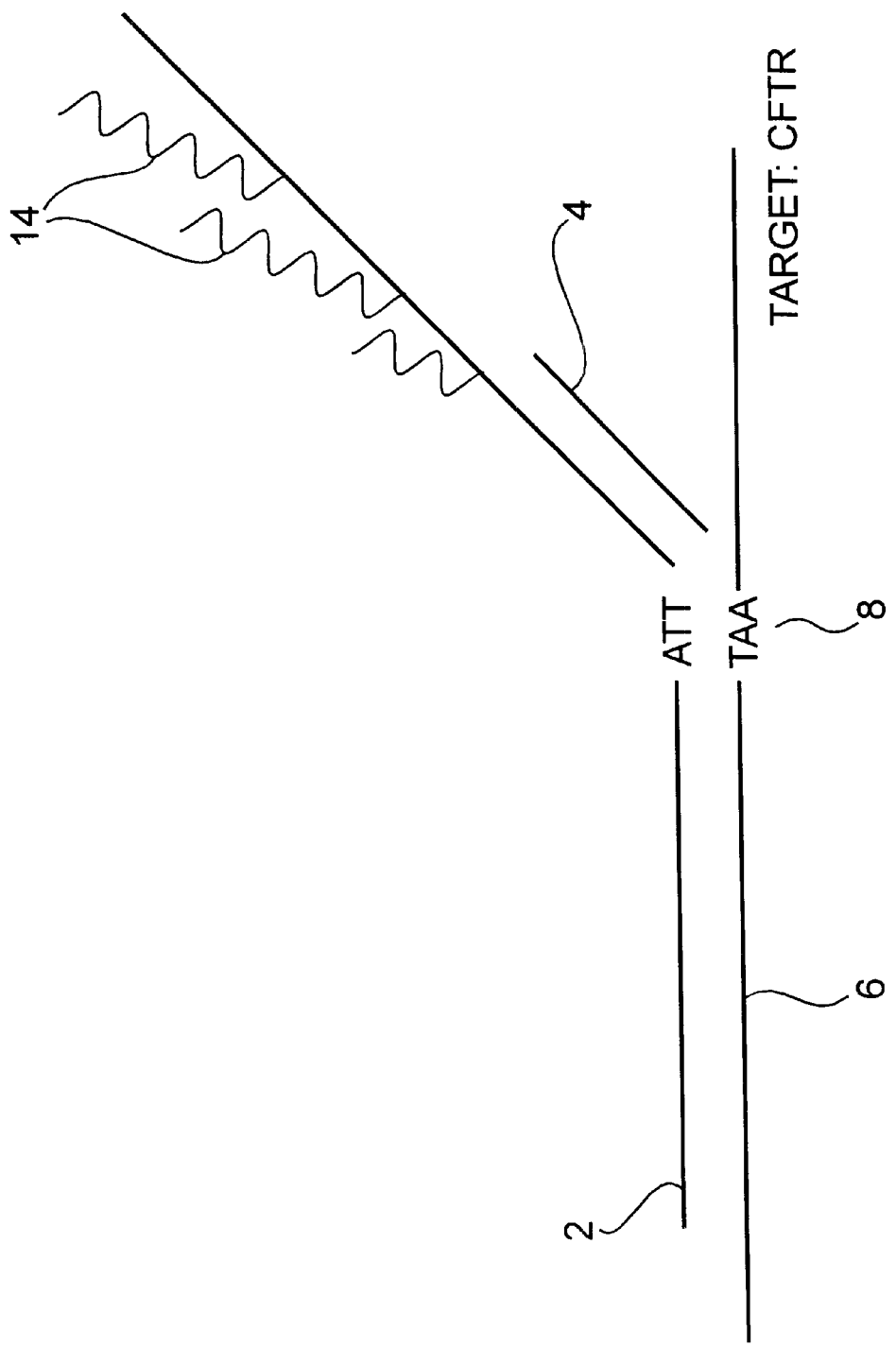

5 µl of reaction sample was added to the reaction mix consisting of 145 µl hybridization buffer (20 mM EDTA pH 8.0, 1 M NaCl, 50 mM Tris, 0.1% bovine serum albumin, mixture adjusted to pH 8.0 with HCl), 0.9 pmol of probe 3 and 12.7 pmol of probe 4 in a well of a Labsystems streptavidin coated microtite plate, which was incubated at room temperature for 60 minutes. Unbound material was removed by washing the wells 4× with 200 µl of wash solution (0.25 M Tris, 0.69 M NaCl, 13.4 mM KCl, adjusted to pH 8.0 with HCl), and 1× with substrate buffer (used as a 1× solution, made from a 5× concentrate stock obtained from Boehringer Mannheim 726915). 180 µl of substrate buffer containing 5 mg/ml of 4-nitrophenyl phosphate was added the well, and colour development was measured by optical density at 405 nm using a Labsystems integrated EIA Management system plate reader, readings taken every 2 minutes for 30 minutes. The results obtained are shown in FIG. 10.

6.4 List of Oligonucleotides

Target oligonucleotide (Normal wild type DNA)

5' GTTGGCATGCTTTGATGACGCTTCTG-TATCTATATTCATCATAGGAAACACC aaaGAT-GATATTTTCT TTAATGGTGCCAGGCATAATCCAGGAAAACTGAA CAGAATGAAATTCTTC 3' (Seq. ID No. 32)

CS Probe (T7 promoter)

5' CAGTTTTCCTGGATTATGCCTGGCACCAT TAATACGACTCACTATA 3' (Seq. ID No. 35)

PS Probe (T7 promoter with 3' ATT 5' start sequence in target, and template portion)

5' CCTTGTCTCCGTTCTGGATATCAC-CCGATGTGTCTCCCTATAGTGAGTCGTA AGAAAATATCATCTTTGGTGTTTCCTATGATG 3' (Seq. ID No. 36)

Probe 3 (with 5' biotin to allow capture on streptavidin coated plates)

5' TGCCTCCTTGTCTCCGTTCT 3' (Seq. ID No. 20)

Probe 4 (alkaline phosphatase-labelled)

5' GGATATCACCCGATGTG 3' (Seq. ID No. 37)

Example 7

Transcription from a Split T7 RNA Polymerase Promoter, and Amplification Without the Use of DNA Polymerase Extension This example demonstrates the creation of a functional DNA dependent RNA polymerase promoter as a result of the formation of a nucleic acid complex comprising target nucleic acid (Target: wild type human DNA: cystic fibrosis transmembrane conductance regulator gene (CFTR) at which a deletion of TTT causes a cystic fibrosis-encoding mutation DF508), a partly complementary oligonucleotide and a promoter strand probe.

Figure 12:
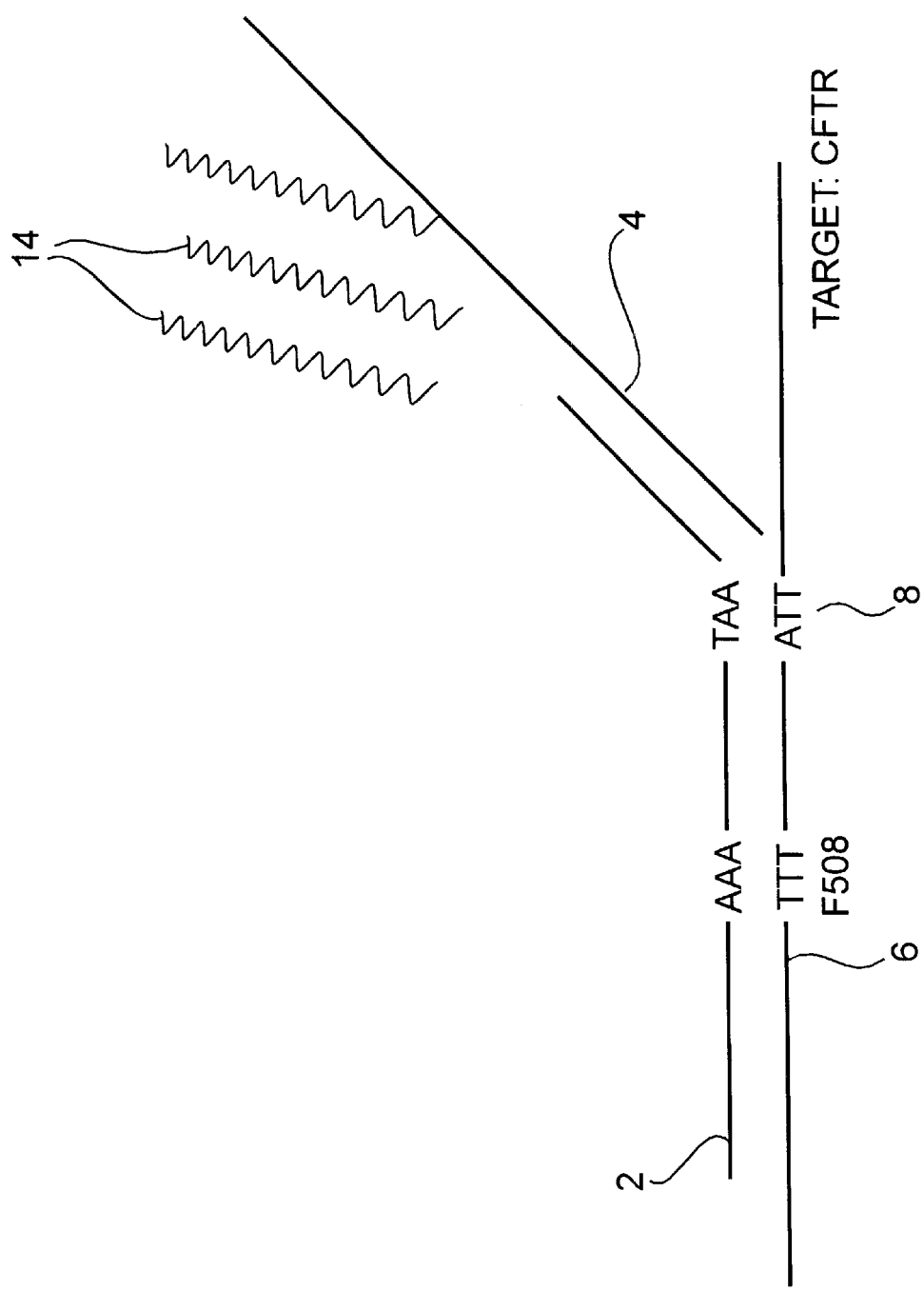

The example is illustrated schematically in FIG. 12. The complete T7 promoter is located towards the 3' end of a CS probe (2). The first three (5') bases of the promoter sequence is complemented by three bases (3' ATT 5') (8) in target (6), and CS probe (2) hybridizes to target (6) in such a way that the 3' TTT 5' in the wild type sequence is 14 bases downstream from the start of the promoter. Hybridization of a PS probe (4), (at the 3' end of which is the complement to the T7 promoter minus three bases) to CS probe (2) forms a double stranded promoter, made complete by the three bases (8) in target (6), and therefore a split promoter is formed to yield a de novo synthesized RNA (14) in the presence of T7 RNA polymerase.

Figure 13:
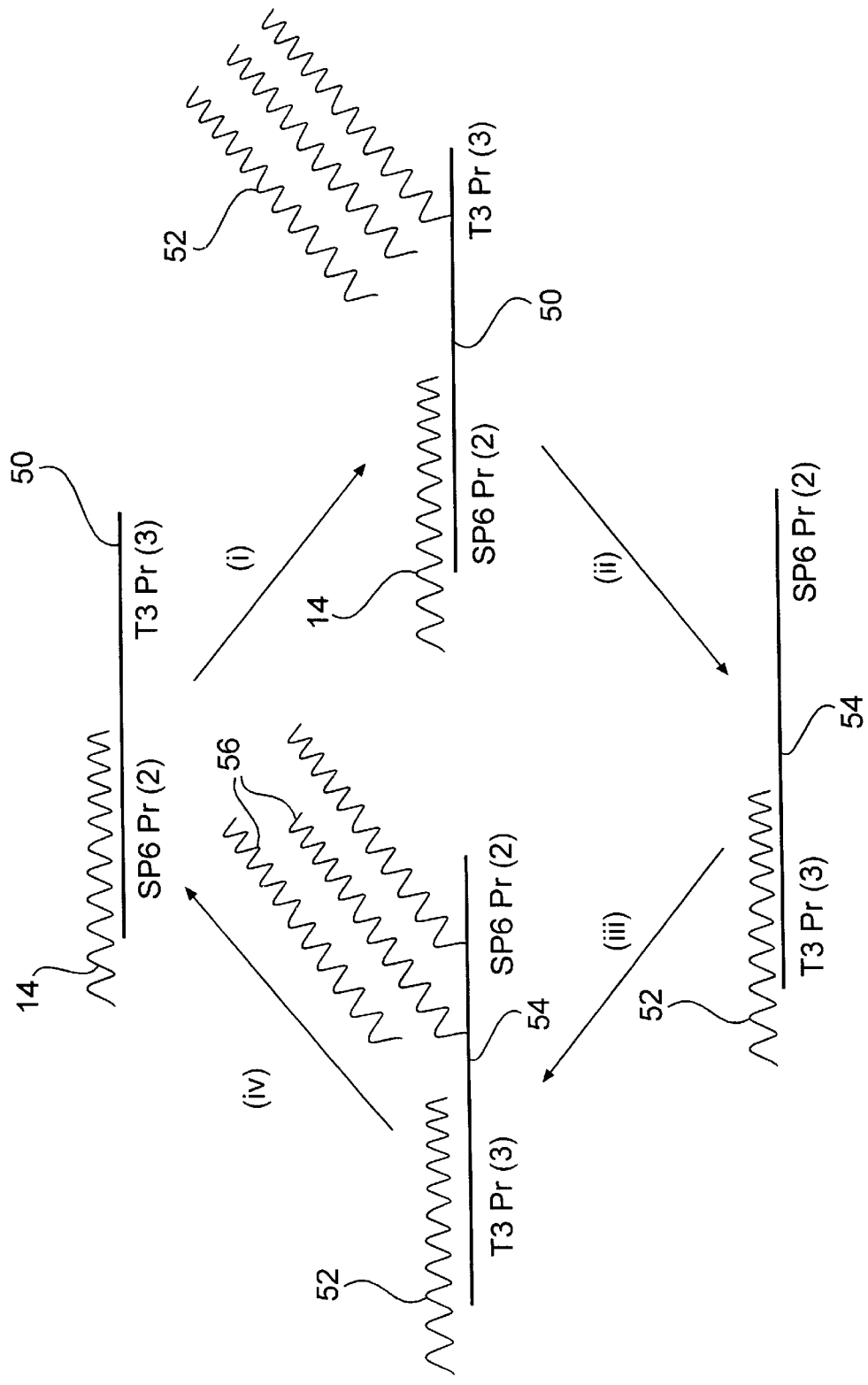

The de novo synthesized RNA species is then amplified, as represented in FIG. 13. Referring to FIG. 13, RNA molecule (14) contains an overlap sequence, a second promoter sequence (SP6, designated as Pr (2) in FIGS. 12 and 13) and a further 6 bases to compensate for possible early termination of transcription. This molecule (14) anneals to added DNA probe 3 (50 in FIG. 13) in the amplification scheme, creating a double stranded SP6 promoter and thus initiates the amplification cycle (step i). The RNA transcript (52) from probe 3 (50) includes a different overlap sequence to that of RNA molecule (14), a sequence for T3 RNA polymerase promoter (promoter 3 or Pr 3) and a further 6 bases. This molecule (52) anneals (step ii) to added DNA probe 4, (54 in FIG. 13) creating a double stranded T3 promoter which initiates the transcription (step iii) of RNA (56) anneals (step iv) to probe 3 (50) in a continuation of the amplification cycle. Note that promoters 1, 2 and 3 need not be necessarily T7, SP6 and T3 RNA polymerase promoters respectively: they could be used in a different order to that shown, or one or more other RNA promoters not discussed here may alternatively be employed.

In contrast to the amplification system illustrated in FIG. 3, an active RNA promoter is formed directly by hybridization of appropriate nucleic acid sequences in the system described above, there is no extension required for promoter formation.

7.1 Preparation of Oligonucleotides

The target oligonucleotides and probes are synthesized and purified as described in Example 1.

7.2 RNA Synthesis by Split Promoter and Amplification Cycle

Hybridization reactions comprise mixtures of DNA including target oligonucleotide, PS and CS probes, probe 3 and probe 4 together with relevant controls comprising mixtures with and without target/PS or CS probes and probes 3 and 4. For hybridization reactions, 40 fmol of target oligonucleotide is mixed with 40 fmol each of probes PS, CS, 3 and 4 in a solution containing 4 µl 5× RNA polymerase buffer (giving 1× concentrations of 40 mM Tris (pH7.9), 6 mM MgCl$_2$, 2 mM spermidine and 10 mM NaCl) and distilled water to a final volume of 20 µl (following final addition of T7, SP6 and T3 RNA polymerases and rNTP mix). The mixture is heated to 90° C. for 3 minutes to denature the nucleic acids, incubated on ice for 2 minutes, and equilibrated to 37° C. for 1 minute. Probes are annealed and transcribed at 37° C. for 180 minutes by addition of 40 units of each RNA polymerase (Promega) and 120 nmoles of each rNTP (Pharmacia Biotech). DNA oligonucleotides are removed from the reaction mix by heating to 90° C. for 3 minutes and incubating on ice for 2 minutes followed by the addition of 4 units of DNase I (Ambion) and incubating at 37° C. for 20 minutes prior to end detection. One (or potentially both) of the resulting products (RNAs 14 & 52) may be detected by the hybridization of molecular beacon (see below).

7.3 Detection of RNA by Molecular Beacon Assay

5 µl of reaction sample was added to the reaction mix consisting of 145 µl of hybridization solution and 2 pmol molecular beacon (5' fluorophore=FAM; 3' quencher= methyl red probe 5), in a Labsystems White Microstrip well plate, which is incubated in the dark at room temperature for 60 minutes. Fluorescence signal from the hybridized beacon/target is measured using the Wallac Victor 1420 Multilabel Counter, using the fluorescein protocol.

7.4 List of Oligonucleotides

Target oligonucleotide (Normal wild type CFTR DNA)

5' TTATGCCTGGCACCA TTAAAGAAATATCATCtttGGTGTTTCCTATGATGA ATATAGATACAGAAGCGTCATCAAAGC 3' (Seq. ID No. 16)

CS probe (T7 promoter)

5' ATAGGAAACACCAAAGATGATATTTTCTTT AATACGACTCACTATA 3' (Seq. ID No. 17)

PS Probe (T7 promoter (Pr1) with 3' ATT 5' start sequence in target, and template portion which encodes transcript with SP6 promoter (Pr2))

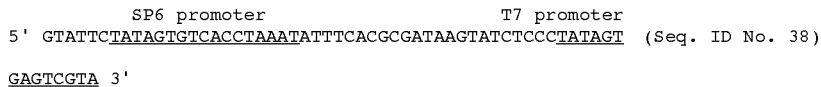

Probe 3 (first DNA oligo in amplification cycle with SP6 promoter (Pr2), encoding transcript with T3 promoter (Pr3))

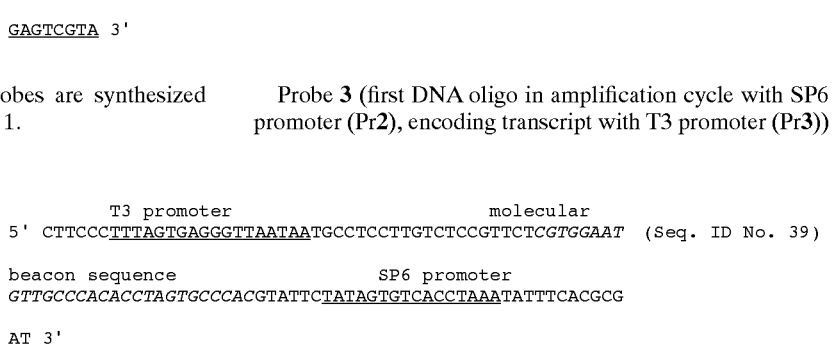

Probe 4 (second DNA oligo in amplification cycle with T3 promoter (Pr3) encoding transcript with SP6 promoter (Pr2))

```
         SP6 promoter              molecular
5' GTATTCTATAGTGTCACCTAAATATTTCACGCGATAAGTACGTGGAATGTTG  (Seq. ID No. 40)

beacon sequence        T3 promoter
CCCACACCTAGTGCCCACCTTCCCTTTAGTGAGGGTTAATAATGCCTCCTTGTCT

CC 3'
```

Probe 5 (molecular beacon: 5' fluorescent label and 3' quencher)
FAM 5' CGCGCGTGGAATGTTGCCCACACCTAGT-GCCCACCGCG 3' Methyl red (Seq. ID No. 41)

Example 8

Transcription from a Split T7 RNA Pol Promoter 2½ Way Junction, Using an RNA Target This example involves the use of an RNA target (based on the CFTR sequence). The complete T7 promoter is located towards the 3' end of CS probe. The first three (5') bases of the promoter sequence is complemented by three bases (3' AUU 5') in the target, when CS probe hybridizes to the target. Hybridization of a second oligonucleotide (PS probe, at the 3' end of which is the complement to the T7 promoter minus three bases) to CS probe forms a double stranded promoter, made complete by the three bases in the target, and therefore a split promoter is formed to yield a de novo synthesized RNA in the presence of T7 RNA polymerase. This reaction was compared to a control reaction which used a DNA version of the CFTR target. This example shows that sample RNA could be used as a target for the split promoter (i.e. that the polymerase will recognize a promoter which comprises at least three bases of RNA rather than DNA). Furthermore, the resulting RNA transcript could be further amplified using a second split promoter. The RNA signal from this second promoter could be again amplified by re-forming the previous split promoter, and so on, in an amplification cycle relying on the presence of T7 RNA polymerase and rNTPs only (e.g. as illustrated schematically in FIG. 15).

8.1 Preparation of Oligonucleotides

The target oligonucleotides and probes were synthesized and purified as described in Example 1.

8.2a Synthesis and Quantification of RNA Target

RNA target molecules were prepared by transcription with T7 RNA polymerase, under standard conditions, of a double stranded DNA oligonucleotide prepared so as to include a T7 polymerase promoter. DNA oligonucleotides were then removed from the reaction mix by addition of 3 units of DNase I (Ambion) and incubation at 37° C. for 10 minutes, followed by heat inactivation of the enzyme at 90° C. for 3 minutes. The transcript was quantified using the RiboGreen RNA Quantitation Kit (Molecular Probes, R-11490).

For quantification, 5 µl of the reaction mixes, or of dilutions in TE were added to 95 µl of TE in the well of a Labsystems White Microstrip well plate, together with 100 µl of the Quantitation Reagent (a 1/2000 dilution of the Quantitation Reagent in TE, according to the manufacturer's instructions). The plate was shaken at 200 rpm for 5 minutes at 22° C., followed by detection of fluorescence signal from the intercalated fluorophore/RNA measured using the Wallac Victor 1420 Multilabel Counter, using the fluorescein protocol. The fluoresence signal value was converted to pmol RNA by comparison to a standard curve measured in the same way as the transcript, but using a standard synthetic RNA (probe 3, below). The quantified RNA was stored in 10 µl aliquots at −80° C.

8.2b Split Promoter Probe and RNA Synthesis

Hybridization reactions comprised mixtures of DNA including target RNA or DNA oligonucleotide, CS probe and PS probe together with relevant controls comprising mixtures with and without target/probes CS and PS. For hybridization reactions, 50 fmol of target RNA or DNA oligonucleotide was mixed with 50 fmol of CS probe and 50 fmol of PS probe in a solution containing 28.3 µl T7 RNA polymerase buffer (giving 1× concentrations of 40 mM Tris (pH8.1), 20 mM MgCl$_2$, 1 mM spermidine, 5 mM DTT (Promega P117C), 80 mg/ml PEG 8000, 50 µg/ml BSA, and 0.01% Triton X-100: Milligan et al., 1987, Nucleic Acids Research, volume 15, pp. 8783–8798) and distilled water to a final volume of 50 µl (following final addition of T7 RNA polymerase and rNTP mix). The mixture was heated to 90° C. for 3 minutes to denature the nucleic acids, then cooled to 10° C. at 0.1° C. per second for hybridization. Probes were annealed and transcribed at 37° C. for 180 minutes by addition of 25 units of T7 RNA polymerase and 40 nmoles of each rNTP. DNA oligonucleotides were removed from the reaction mix by the addition of 3 units of DNase I and incubating at 37° C. for 10 minutes, followed by heating to 90° C. for 3 minutes, and cooling to 15° C., prior to end detection. The resulting product was immobilised by hybridization to a specific biotinylated oligonucleotide (probe 4, below) which was in turn bound to a streptavidin coated well. The immobilised product was detected by colorimetry via the hybridization of probe 5 (see below), an alkaline phosphatase-labelled oligonucleotide probe.

8.3 Detection of RNA by Colorimetry

5 µl of reaction sample or dilutions was added to the reaction mix consisting of 145 µl hybridization buffer (20 mM EDTA pH 8.0, 1 M NaCl, 50 mM Tris, 0.1% bovine serum albumin, mixture adjusted to pH 8.0 with HCl), 0.9 pmol of probe 4 and 6 pmol of probe 5 in a Labsystems streptavidin coated well plate, which was incubated at 22° C. for 60 minutes. Unbound material was removed by washing the wells 4× with 200 µl of wash solution (0.25 M Tris, 0.69 M NaCl, 13.4 mM KCl, adjusted to pH 8.0 with HCl), and 1× with substrate buffer (used as a 1× solution, made from a 5× concentrate stock obtained from Boehringer Mannheim). 180 µl of substrate buffer containing 5 mg/ml of 4-nitrophenyl phosphate was added to the well, and colour development was measured by optical density at 405 nm using a Labsystems integrated EIA Management system plate reader, readings taken every 2 minutes for 30 minutes. Results are shown in FIG. 14.

Figure 14:
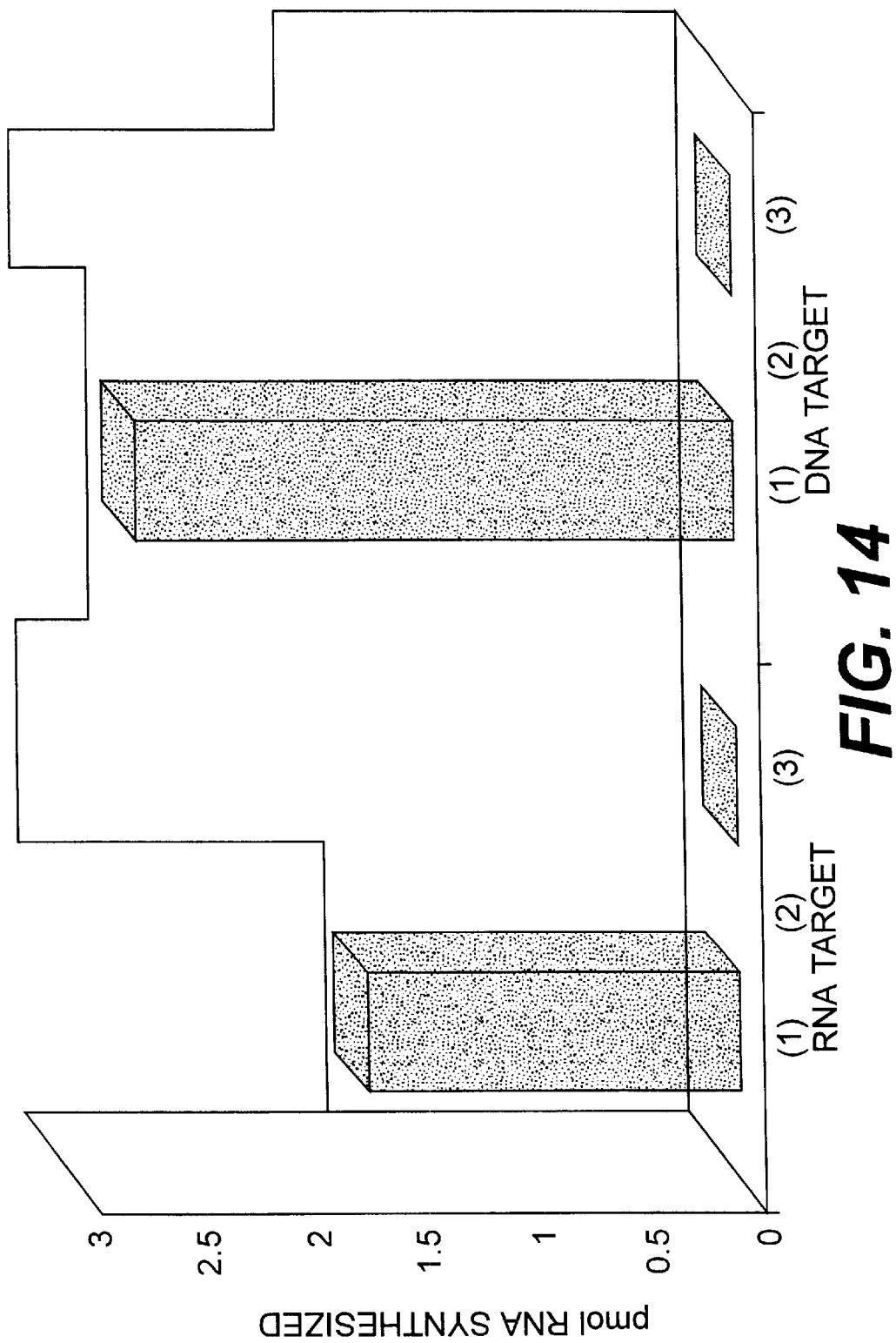

FIG. 14 is a bar chart showing the amount of RNA produced (in picomoles) using either an RNA target (left hand columns) or a DNA target (right hand columns). For each group of columns, (1) gives the results obtained for mixtures comprising target and first and second probes; (2) gives the results obtained in the absence of target; and (3) gives the results obtained in the absence of target and first probe.

It can be seen that, although a DNA target results in the production of more RNA, both DNA and RNA targets can be used successfully to form functional "split" promoters. In either case the background signal is very low.

8.4 List of Oligonucleotides

RNA target (sequence based on normal wild type CFTR DNA) (Seq. ID No. 42)

5'GGGAGAUGAUGACGCUUCUGUAUCUAUA-UUCAUCAUAGGAAACACCAAAGA UGAUAU-UUUCU
UUAAUGGUGCCAGGCAUAAUCCAGGAAAA CUGAGAACA3'

DNA target oligonucleotide (Normal wild type CFTR DNA)

5'GTTGGCATGCTTTGATGACGCTTCTG-TATCTATATTCATCATAGGAAACACCAA AG ATGATATTTTCT
TTAATGGTGCCAGGCATAATCCAGGAAAACT GAGAACAGAA TGAAATTCTTC3' (Seq. ID No. 32)

CS probe (T7 promoter with complementary 3' ATT5' start sequence in target)

5'CAGTTTTCCTGGATTATGCCTGGCACCAT TAATACGACTCACTATA3' (Seq. ID No. 35)

PS probe (T7 promoter and template)

5'TGCCTCCTTGTCTCCGTTCTGGATAT-CACCCGATGTGTCTCCCTATAGTGAGTCGTA3' (Seq. ID No. 19)

Probe 3 (RNA control for constructing the standard curve in the RiboGreen assay)

5'GGGAGACACAUCGGGUGAUAUCCA-GAACGGAGACAAGG3' (Seq. ID No. 43)

Probe 4 (with 5' biotin to allow capture on streptavidin coated plates)

5'TCCGCTGCCTCCTTGTCTCCGTTCT3' (Seq. ID No.21)

Probe 5 (alkaline phosphatase-labelled)

5'GGATATCACCCG3' (Seq. ID No.22)

Example 9

Transcription of a Ribozyme from a Split T7 RNA Pol Promoter at a 2½ Way Junction In this example RNA produced from a split promoter has the sequence of a known ribozyme (Clouet-D'Orval & Uhlenbeck, 1996 RNA 2(5):483–491) and can bind to a dual labelled single stranded oligonucleotide to form a functional ribozyme. Cleavage of the labelled oligonucleotide at a specific site will then generate a signal. The complete T7 promoter is located towards the 3' end of CS probe. The first three (5') is bases of the promoter sequence is complemented by three bases (3' ATT 5') in the target, when CS probe hybridizes to the target. Hybridization of a second oligonucleotide (PS probe, at the 3' end of which is the complement to the T7 promoter minus three bases) to CS probe forms a double stranded promoter, made complete by the three bases in the target, and therefore a split promoter is formed to yield a de novo synthesized RNA ribozyme in the presence of T7 RNA polymerase.

9.1 Preparation of Oligonucleotides

The target oligonucleotides and probes are synthesized and purified as described in Example 1.

9.2 Split Promoter Probe and RNA Synthesis

Hybridization reactions comprise mixtures of DNA including target oligonucleotide, CS probe and PS probe together with relevant controls comprising mixtures with and without target/probes CS and PS. For hybridization reactions, 40 fmol of target oligonucleotide is mixed with 40 fmol of CS probe and 40 fmol of PS probe in a solution containing 4 µl 5× T7 RNA polymerase buffer (giving 1× concentrations of 40 mM Tris (pH7.9), 6 mM MgCl$_2$, 2 mM spermidine and 10 mM NaCl) and distilled water to a final volume of 20 µl (following final addition of T7 RNA polymerase and rNTP mix). The mixture is heated to 90° C. for 3 minutes to denature the nucleic acids, then cooled to 10° C. at 0.1° C. per second for hybridization. Probes are annealed and transcribed at 37° C. for 180 minutes by addition of 40 units of T7 RNA polymerase and 40 nmoles of each rNTP. DNA oligonucleotides are removed from the reaction mix by the addition of 3 units of DNase I and incubating at 37° C. for 20 minutes prior to end detection.

9.3 Detection of Synthesized RNA

5 µl aliquots of sample or 5 µl of a suitable dilution of the treated assay sample are added to 100 µl buffer (50 mM Tris-HCl pH7.5, 20 mM MgCl$_2$, 10% ethanol), followed by 10 pmol probe 3. This double-labelled RNA (5'-Tamra, 3'-Fam) is the ribozyme substrate. The RNA product of the 2½ way junction (formed in the presence of specific target) is designed to be the corresponding "hammerhead" ribozyme. Probe 3 therefore anneals to the RNA product, creating a functional ribozyme. Ribozyme cleavage of the substrate, which results in the removal of the quencher from the fluorophore, can be monitored by Fluorescence Resonance Energy Transfer (Tamra excitation at 546 nm, emission at 579 nm). Alternatively, substrate cleavage could be measured by a decrease in fluorescence polarisation. Since substrate turnover is possible, a level of amplification may be achieved during the detection process.

Alternative Real Time Detection System

Real time detection would be possible if the ribozyme substrate molecule is included in the extension/transcription reaction mixture, under suitable buffer conditions.

Alternative Detection Systems:

The RNA product could include a capture sequence, allowing it to be captured on to a streptavidin-coated well via a biotinylated capture probe. After wash steps to remove unbound material, probe 3 could be added and ribozyme cleavage could be monitored as described above.

Alternative labels could be attached to the ribozyme substrate molecule.

9.4 List of Oligonucleotides

Target oligonucleotide (Normal wild type CFTR DNA)

5'GTTGGCATGCTTTGATGACGCTTCTG-TATCTATATTCATCATAGGAAACACCaa aGAT-GATATTTTCT
TTAATGGTGCCAGGCATAATCCAGGAAAACT GAGAACAGAA TGAAATTCTTC3' (Seq. ID No. 32)

CS probe (T7 promoter with 3'ATT5' start sequence in target)

5'CAGTTTTCCTGGATTATGCCTGGCACCAT TAATACGACTCACTATA3' (Seq. ID No. 35)

PS probe (T7 promoter and template, which encodes the ribozyme)

5'GAATCTCATCAGTAGCGAGTTCTCTCTCCC TATAGTGAGTCGTA3' (Seq. ID No. 44)

Probe 3 (ribozyme substrate)

5'Tamra-GAAUCGAAACGCGAAAGCGUCUAGCGU-FAM3' (Seq. ID No. 45)

Example 10

An experiment was conducted to determine the optimum sequence of +12 region for most efficient transcription by T7 RNA polymerase.

Accordingly a series of second probe molecules were prepared, each comprising identical T7 promoter, detection and capture sequences but having different +12 sequences adjacent to the T7 promoter sequence. These probes were hybridized to a complementary 22 base oligonucleotide (containing the complementary strand of the T7 promoter) under identical conditions and the amount of RNA produced was determined as described in the previous examples.

Table 2 below shows the relative "RNA transcription factor" for each of the different +12 sequences tested.

TABLE 2

Alternative template T7 +1 to +12 sequences in descending order of transcription efficiency.

| +1 to +12 sequence | RNA transcription factor |
| --- | --- |
| 5' GTTCTCTCTCCC 3' | 142 |
| 5' GCTCTCTCTCCC 3' | 115 |
| 5' GTTGTGTCTCCC 3' | 110 |

TABLE 2-continued

Alternative template T7 +1 to +12 sequences in descending order of transcription efficiency.

| +1 to +12 sequence | RNA transcription factor |
| --- | --- |
| 5' GATGTGTCTCCC 3' | 105 |
| 5' ATCCTCTCTCCC 3' | 96 |
| 5' GTTCTCGTGCCC 3' | 84 |
| 5' ATCCTCGTGCCC 3' | 76 |
| 5' GCTCTCGTGCCC 3' | 64 |
| 5' GTTGTGGTGCCC 3' | 21 |

What is claimed is:

1. A method of detecting the presence of a nucleic acid target sequence of interest, the method comprising the steps of:
   (a) adding first and second nucleic acid probes to a sample comprising the sequence of interest, so as to form a complex comprising three strands of nucleic acid, wherein the first probe comprises the full length sequence of a first strand of a double stranded promoter, the target sequence comprises an end part of a second strand of the double stranded promoter which is complementary to a part of the first strand, and the second probe comprises the rest of the second strand of the double stranded promoter which is complementary to a part of the first strand, such that a functional promoter is formed when the first probe is hybridized to both the target sequence and to the second probe;
   (b) adding a polymerase which recognizes the promoter, so as to cause the de novo synthesis of nucleic acid from the promoter present in the complex; and
   (c) detecting directly or indirectly the de novo synthesized nucleic acid.

2. A method according to claim 1, wherein the promoter is an RNA polymerase promoter and the de novo synthesized nucleic acid is RNA.

3. A method according to claim 1, wherein the promoter is recognized by T3, T7 or SP6 RNA polymerase.

4. A method according to any one of the preceding claims, wherein the second probe comprises a template portion which may act as a template for synthesis of nucleic acid from the functional promoter.

5. A method according to claim 4, wherein the second probe comprises a +12 region adjacent to the promoter to optimize transcription from the promoter.

6. A method according to claim 5, wherein the second probe comprises a +12 region sequence selected from the group consisting of:

(5'®3') GTTCTCTCTCCC; GCTCTCTCTCCC; GTTGTGTCTCCC; GATGTGTCTCCC; ATCCTCTCTCCC; GTTCTCGTGCCC; ATCCTCGTGCCC; GCTCTCGTGCCC; and GTTGTGGTGCCC.

7. A method according to any one of claims 4, 5 or 6, wherein the template portion, when copied by the polymerase, provides a sequence which can act as an RNA polymerase promoter, or may be used for detection and/or capture at a solid surface.

8. A method according to any one of claims 4–7, wherein the template portion, when copied by the polymerase, provides a sequence which hybridizes with a molecular beacon.

9. A method according to claim 4, wherein the template portion, when copied by the polymerase, provides a sequence which is a ribozyme.

10. A method according to any one of the preceding claims, wherein the de novo synthesized nucleic acid is subjected to an amplification step prior to detection.

11. A method according to claim 10, wherein the amplification step comprises: hybridizing the de novo synthesized nucleic acid to a third nucleic acid probe, which hybridization forms a second double stranded nucleic acid promoter either directly, or by 3' extension of the de novo synthesized nucleic acid using the third probe as template; and adding a polymerase which recognizes the second promoter so as to cause nucleic acid synthesis therefrom.

12. A method according to claim 10, wherein the nucleic acid synthesized from the second promoter is detected.

13. A method according to claim 11, further comprising the steps of: hybridizing the nucleic acid synthesized from the second promoter to a fourth nucleic acid probe, which hybridization forms a third double stranded nucleic acid promoter either directly, or by 3' extension of the nucleic acid synthesized from the second promoter using the fourth probe as a template; and adding a polymerase which recognizes the third promoter thereby causing nucleic acid synthesis therefrom.

14. A method according to claim 13, wherein nucleic acid synthesized from the third promoter is detected.

15. A method according to claim 13, further comprising the step of hybridizing nucleic acid synthesized from the third promoter to the third probe, thereby reforming the second double stranded promoter, so as to create a cycle of nucleic acid synthesis.

16. A method according to claim 10, wherein the amplification step comprises: adding third and fourth nucleic acid probes to form a complex comprising said probes and the de novo synthesized nucleic acid, wherein the third probe comprises the full length sequence of a first strand of a double stranded promoter, the de novo synthesized nucleic acid comprises an end part of a second strand of the double stranded promoter which is complementary to a part of the first strand, and the fourth probe comprises the rest of the second strand of the double stranded promoter which is complementary to a part of the first strand, such that a functional promoter is formed when the third probe is hybridized to both the de novo synthesized nucleic acid and to the fourth probe; adding a polymerase which recognizes the promoter, so as to cause the synthesis of nucleic acid from the promoter present in the complex; and detecting directly or indirectly the synthesized nucleic acid.

17. A nucleic acid complex comprising three strands of nucleic acid: a promoter strand, a promoter complementary strand, and a target strand; wherein the promoter complementary strand comprises the full length sequence of a first strand of a double stranded promoter; the target strand comprises a part of a second strand of the double stranded promoter which is complementary to a part of the first strand; and the promoter strand comprises a part of the second strand of the double stranded promoter which is complementary to a part of the first strand; wherein neither part of the second strand of the double stranded promoter present on the target strand or on the promoter strand is capable of forming a functional promoter when hybridized to the promoter complementary strand in the absence of the other part, but wherein a functional promoter is formed when the promoter complementary strand is hybridized to both the target strand and the promoter strand.

18. A complex according to claim 17, wherein the promoter complementary strand and promoter strand are provided by first and second nucleic acid probes respectively, the complex being formed in performance of a method comprising:

(a) adding first and second nucleic acid probes to a sample comprising the sequence of interest, thereby forming a complex comprising three strands of nucleic acid, wherein the first probe comprises a full length sequence of a first strand of a double stranded promoter, the target sequence comprises an end part of a second strand of the double stranded promoter which is complementary to a part of the first strand, and the second probe comprises the rest of the second strand of the double stranded promoter which is complementary to a part of the first strand, such that a functional promoter is formed when the first probe is hybridized to both the target sequence and to the second probe;

(b) adding a polymerase which recognises the promoter, thereby causing de novo synthesis of nucleic acid from the promoter Present in the complex; and (c) detecting directly or indirectly the de novo synthesised nucleic acid.

19. A kit comprising:

first and second probes for forming, together with an appropriate target sequence, a nucleic acid complex comprising:

three strands of nucleic acid: a promoter strand, a promoter complementary strand, and a target strand; wherein the promoter complementary strand comprises a full length sequence of a first strand of a double stranded promoter; the target strand comprises a part of a second strand of the double stranded promoter which is complementary to a part of the first strand; and the promoter strand comprises a part of the second strand of the double stranded promoter which is complementary to a part of the first strand;

wherein neither part of the second strand of the double stranded promoter present on the target strand or on the promoter strand forms a functional promoter when hybridized to the promoter complementary strand in the absence of the other part, but wherein a functional promoter is formed when the promoter complementary strand is hybridized to both the target strand and the promoter strand, and instructions for performing the method.

20. A kit according to claim 19, further comprising at least one member selected from the group consisting of: DNA polymerase, RNA polymerase, ribo- or deoxyribonucleotide triphosphates, labelling reagents, detection reagents, and buffers.

21. A method according to claim 1, wherein the second probe does not comprise a sequence which hybridizes to the target sequence under the assay conditions employed.

22. A method according to claim 1, wherein the first probe comprises a target-specific sequence which comprises LNA or PNA.

* * * * *